(12) United States Patent
Klinman et al.

(10) Patent No.: US 10,076,535 B2
(45) Date of Patent: Sep. 18, 2018

(54) USE OF CPG OLIGONUCLEOTIDES CO-FORMULATED WITH AN ANTIBIOTIC TO ACCELERATE WOUND HEALING

(71) Applicant: THE UNITED STATES OF AMERICA, as represented by the Secretary, Department of Health and Human Services, Washington, DC (US)

(72) Inventors: Dennis M. Klinman, Potomac, MD (US); Hiroyasu Ito, Gifu (JP)

(73) Assignee: THE UNITED STATES OF AMERICA, as represented by the Secretary, Department of Health and Human Services, Washington, DC (US)

( * ) Notice: Subject to any disclaimer, the term of this patent is extended or adjusted under 35 U.S.C. 154(b) by 274 days.

(21) Appl. No.: 14/397,156

(22) PCT Filed: Mar. 29, 2013

(86) PCT No.: PCT/US2013/034639
§ 371 (c)(1),
(2) Date: Oct. 24, 2014

(87) PCT Pub. No.: WO2013/162828
PCT Pub. Date: Oct. 31, 2013

(65) Prior Publication Data
US 2015/0104482 A1    Apr. 16, 2015

Related U.S. Application Data

(60) Provisional application No. 61/639,688, filed on Apr. 27, 2012.

(51) Int. Cl.
| | |
|---|---|
| *A61K 38/12* | (2006.01) |
| *A61K 39/00* | (2006.01) |
| *A61K 9/00* | (2006.01) |
| *A61K 31/713* | (2006.01) |
| *A61K 31/4745* | (2006.01) |
| *A61K 31/711* | (2006.01) |
| *A61K 31/7036* | (2006.01) |
| *A61K 9/06* | (2006.01) |

(52) U.S. Cl.
CPC .......... *A61K 31/713* (2013.01); *A61K 9/0014* (2013.01); *A61K 9/0048* (2013.01); *A61K 9/06* (2013.01); *A61K 31/4745* (2013.01); *A61K 31/7036* (2013.01); *A61K 31/711* (2013.01); *A61K 38/12* (2013.01)

(58) Field of Classification Search
None
See application file for complete search history.

(56) References Cited

U.S. PATENT DOCUMENTS

| | | | | |
|---|---|---|---|---|
| 7,521,063 B2* | 4/2009 | Klinman | ............ | C12N 15/117 424/278.1 |
| 7,615,227 B2* | 11/2009 | Klinman | ............ | C12N 15/117 424/198.1 |
| 7,935,351 B2* | 5/2011 | Klinman | ............ | C12N 15/117 424/184.1 |
| 7,959,934 B2* | 6/2011 | Klinman | ............ | A61K 39/39 424/184.1 |
| 9,919,058 B2* | 3/2018 | Klinnnan | ............ | A61K 31/475 |
| 2004/0131628 A1 | 7/2004 | Bratzler | | |
| 2009/0099122 A1 | 4/2009 | Klinman | | |
| 2009/0304812 A1 | 10/2009 | Staniforth et al. | | |
| 2010/0278784 A1 | 11/2010 | Pojasek et al. | | |
| 2015/0104482 A1* | 4/2015 | Klinman | ............ | A61K 38/12 424/278.1 |
| 2017/0202977 A1* | 7/2017 | Klinman | ......... | A61K 47/48907 |

FOREIGN PATENT DOCUMENTS

| WO | WO 2003/054161 A2 | 7/2003 |
|---|---|---|
| WO | WO 2006/063072 A2 | 6/2006 |

OTHER PUBLICATIONS

Verthelyi et al., "CpG oligodeoxynucleotides improve the response to hepatitis B immunization in healthy and SIV-infected rhesus macaques," *AIDS* 18:1-6 (2004).
Verthelyi et al., "CpG Oligodeoxynucleotides Protect Normal and SIV-Infected Macaques from Leishmania Infection," *Journal of Immunology* 170: 4717-4723 (2003).
Verthelyi et al., "Human peripheral blood cells differentially recognize and respond to two distinct CpG motifs," *Journal of Immunology* 166: 2372-2377 (2001).
MAXITROL™ Sterile Ophthalmic suspension and ointment, printed from URL:http://web.archive.org/web/20101219001455/http:// medsafe.govt.nz/Profs/Datasheet/m/Maxitroleyedropsoint.pdf (2010).
Berghöfer et al., "Natural and Synthetic TLR7 Ligands Inhibit CpG-A- and CpG-C-Oligodeoxynucleotide-Induced IFN-α Production," *Journal of Immunology* 178: 4072-4079 (2007).
Dockrell and Kinghorn "Imiquimod and resiquimod as novel immunomodulators," *Journal of Antimicrobial Chemotherapy* 48:751-755 (2001).

(Continued)

*Primary Examiner* — Nita M Minnifield
(74) *Attorney, Agent, or Firm* — Klarquist Sparkman, LLP

(57) ABSTRACT

Pharmaceutical compositions are provided that include an antibiotics, but that include ingredients that counteract the effect of that antibiotic on wound healing, without altering the bactericidal properties of the antibiotic. These pharmaceutical compositions include an effective amount of 1) an imidazoquinoline having toll-like receptor 7 (TLR7) ligand activity, 2) an immunostimulatory K-type CpG oligodeoxynucleotide (ODN) comprising an unmethylated CpG motif, 3) an antibiotic, and 4) a surfactant, wherein the composition is formulated for topical administration. Methods for accelerating wound healing are also provided. These methods include topically administering the disclosed compositions. The wound can be in the skin or in the eye.

28 Claims, 7 Drawing Sheets

Specification includes a Sequence Listing.

(56) References Cited

OTHER PUBLICATIONS

Drugs.com, "Maxitrol ophthalmic suspension," Retrieved from the Internet: URL:http://web.archive.org/web/20120128230619/http://www.drugs.com/pro/maxi trol-ophthalmic-suspension.html, 6 pages, (retrieved on Jun. 11, 2013)(whole document 28 Jan. 28, 2012).

International Search Report from parent PCT Application No. PCT/US2013/034639, 5 pages (dated Jul. 5, 2013).

Ito et al., "Antibiotics delay wound healing: an effect reversed by co-administering TLR 7 and 9 Ligands," *Current Angiogenesis* 1:46-51 (2012).

Marshall et al., "Negative regulation of TLR9-mediated IFN-α induction by a small-molecule, synthetic TLR7 ligand," *Journal of Leukocyte Biology* 82: 497-508; (Sep. 2007).

Maxitrol™ "Sterile ophthalmic suspension and ointment," Retrieved from the Internet: URL:http://web.archive.org/web/20101219001455/http://medsafe.govt.nz/Profs/Datasheet/m/Maxi troleyedropsoint.pdf, 3 pages (Jan. 28, 2012).

Robbins and Neal, "Prognosis and treatment of actinic keratosis," *Johns Hopkins Advanced Studies in Medicine* 6(8A):S791-S794 (Sep. 2006).

Sato et al., "Accelerated wound healing mediated by activation of toll-like receptor 9," *Wound Repair Regen.* 18(6): 586-593 (2010).

Shirota et al., "Intra-tumoral injection of CpG oligonucleotides induces the differentiation and reduces the immunosuppressive activity of myeloid-derived suppressor cells," *J. Immunol.* 188(4): 1592-1599 (Feb. 15, 2012).

van den Boorn et al., "Effective melanoma immunotherapy in mice by the skin-depigmenting agent monobenzone and the adjuvants imiquimod and CpG," *PLoS One* 5(5)(e10626): 1-12 (May 2010).

Written Opinion from parent PCT Application No. PCT/US2013/034639, 9 pages (dated Jul. 5, 2013).

Yamamoto et al., "The acceleration of wound healing in primates by the local administration of immunostimulatory CpG oligonucleotides," *Biomaterials* 32: 4238-4242 (2011).

\* cited by examiner

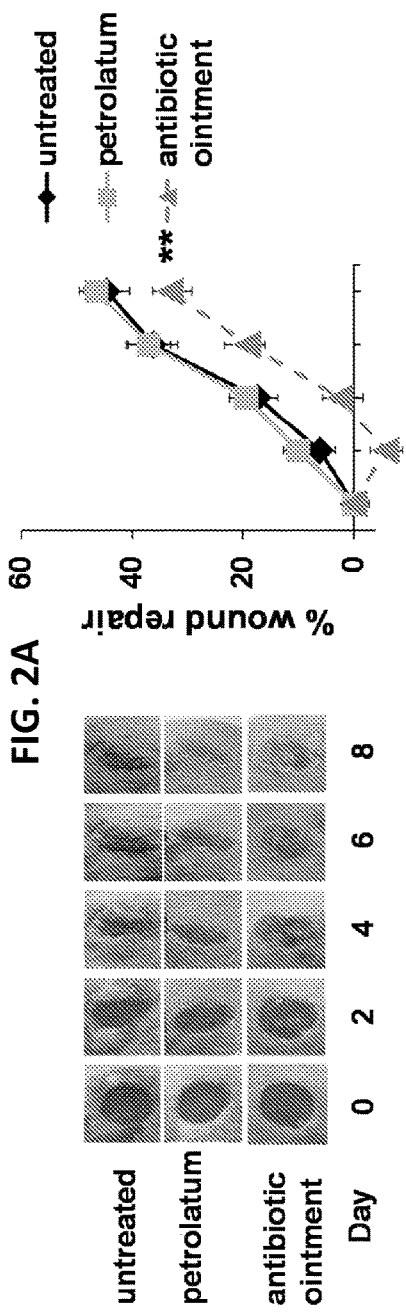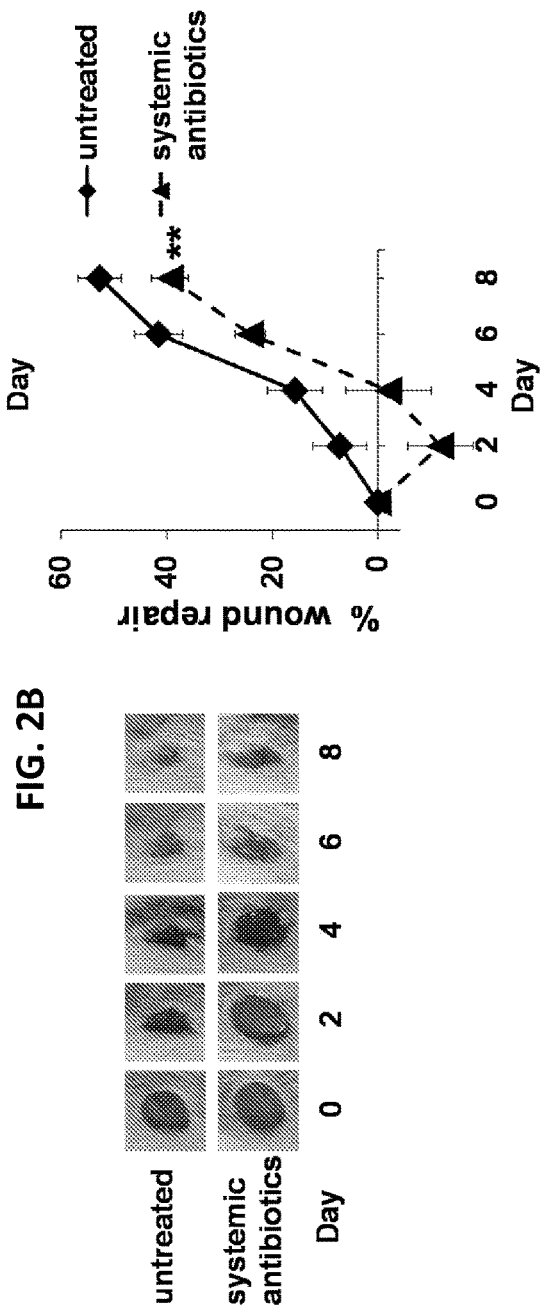
FIG. 2A
FIG. 2B

Fig. 3
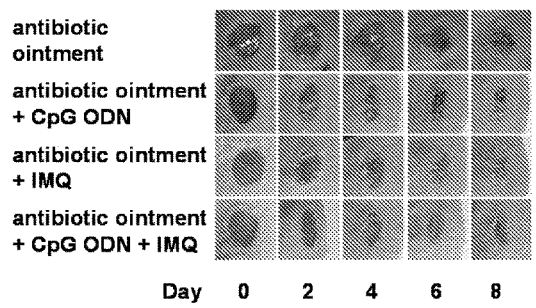
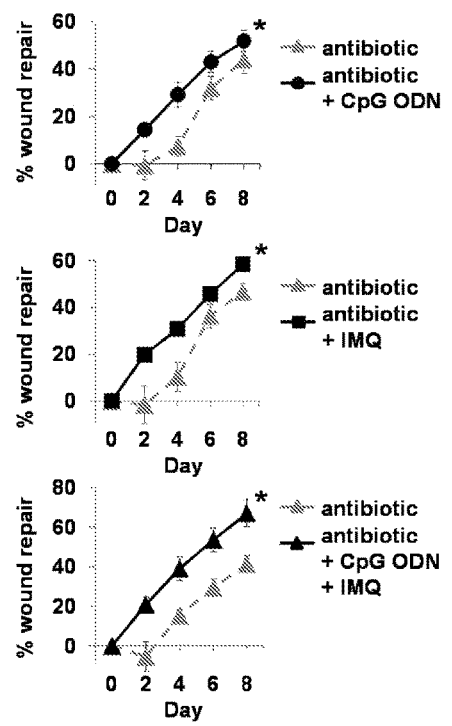

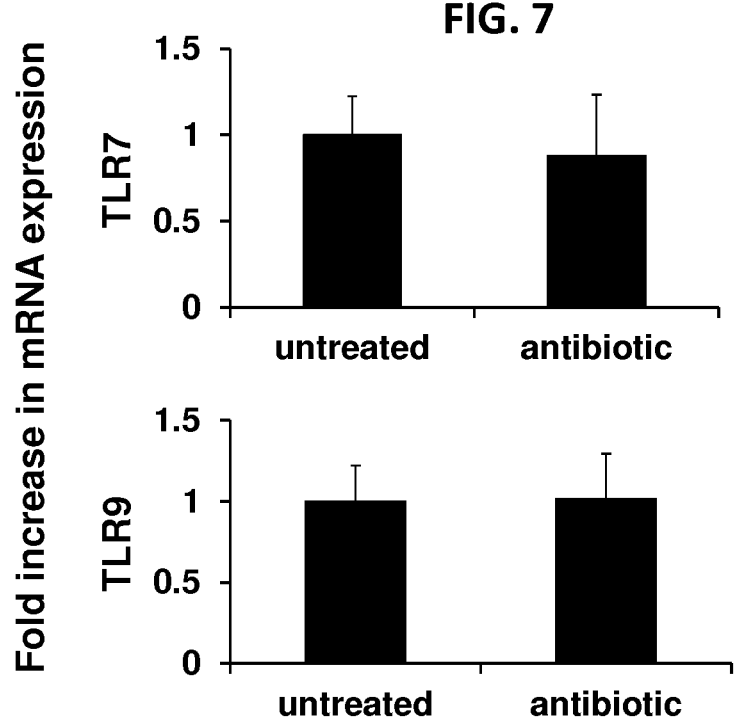

USE OF CPG OLIGONUCLEOTIDES CO-FORMULATED WITH AN ANTIBIOTIC TO ACCELERATE WOUND HEALING

CROSS REFERENCE TO RELATED APPLICATION

This is the U.S. National Stage of PCT Application No. PCT/US2013/034639 filed Mar. 29, 2013, which was published in English under PCT Article 21(2), which claims the benefit of U.S. Provisional Application No. 61/639,688, filed on Apr. 27, 2012, which is incorporated herein by reference in its entirety.

FIELD OF THE DISCLOSURE

This is related to the field of wound healing, specifically to the use of an antibiotic, a K-type CpG oligodeoxynucleotide (ODN), and an imidazoquinoline compound, such as imiquimod or resiquimod, to accelerate wound healing.

BACKGROUND

The skin provides a barrier that protects the host from environmental pathogens. A break in this barrier increases susceptibility to life-threatening infection. When invasive microorganisms gain entry to the host, circulating immune cells and local epithelial cells use Toll-like receptors (TLR) to recognize 'pathogen associated molecular patterns' (PAMPs), and thereby initiate a protective response (Kawai et al., Immunity 2011; 34: 637-50). Recent studies show that stimulating the innate immune system serves an additional function: it accelerates wound repair. Specifically, TLR4 ligands and TLR9 ligands promote healing by inducing the production of cytokines, chemokines, and growth factors that act on inflammatory and epithelial cells at the wound site (see, for example, Sato et al., Wound Repair Regen 2010; 18: 586-93; Koff et al., J Immunol 2006; 177: 8693-700; Yamamoto et al., Biomaterials 2011; 32: 4238-42).

Wound repair is a dynamic process that involves a complex interaction between resident and infiltrating cells, extracellular matrix molecules, and soluble factors. Tissue healing proceeds in three overlapping phases: inflammation, tissue formation, and tissue remodeling (Singer and Clarke, N Engl. J. Med 1999; 341: 738-46). These events are influenced by cytokines and chemokines, including IL-1β and CCL2, that are produced during the inflammatory phase and speed wound healing (Barrients et al., Wound Repair Regen 2008; 16: 585-601; Eming et al., J Invest Dermatol 2007; 127: 514-25). IL-1β is produced by neutrophils, monocytes and macrophages, and functions to increase keratinocyte migration/proliferation and activate fibroblasts (Raja et al., Front Biosci 2007; 12: 2849-68; Kormine et al., J Biol Chem 2000; 275: 32077-88). Inhibition of IL-1 signaling decreases the production of IL-6 and TNFa, suggesting that IL-1 plays a pivotal role during the inflammatory phase of wound healing (Hu et al., *Anesth Analg* 2010; 111: 1525-33). The chemokine CCL2 is also an active participant in the wound healing process (Barrientos et al., Wound Repair Regen 2008; 16: 585-601). CCL2 influences both the recruitment of inflammatory cells and the production of other factors that support wound healing (Raja et al., supra; Christopherson and Hromas, Stem Cells 2001; 19: 388-96). In this context, wound healing is significantly delayed in CCL2 KO mice, as manifested by delayed re-epithelialization, angiogenesis and collagen synthesis (Low et al., Am J Pathol 2001; 159: 457-63). Interferon (IFN) a and IFNb levels also increase at wound sites, where they promote epidermal regeneration and wound repair (Gregoria et al. J Exp Med 2010; 207: 2921-30; Lin et al., J Immunol 2011; 186: 3710-7).

Efforts to reduce wound infection generally rely on local antibiotic treatment to eliminate contaminating bacteria. However, since bacterial PAMPS stimulate an innate immune response that accelerates wound repair, sterilizing the wound might reduce PAMP concentrations and thus indirectly slow healing. A need remains for agents that can increase wound healing in the presence of antibiotics.

SUMMARY OF THE DISCLOSURE

An antibiotic can delay wound healing. Pharmaceutical compositions are provided that include an antibiotic, and include ingredients that counteract the effect of that antibiotic on wound healing, without altering the bactericidal properties of the antibiotic. These pharmaceutical compositions include an effective amount of 1) an imidazoquinoline having toll-like receptor 7 (TLR7) ligand activity, 2) an immunostimulatory K-type CpG oligodeoxynucleotide (ODN) comprising an unmethylated CpG motif, 3) an antibiotic, and 4) a surfactant, wherein the composition is formulated for topical administration. The amount of the ODN and imidazoquinoline are sufficient to counteract the wound healing delay that would otherwise be caused by the antibiotic.

Methods for accelerating wound healing are also provided. These methods include topically administering the disclosed compositions. In some embodiments the wound can be in the skin or in the eye.

The foregoing and other features and advantages of the invention will become more apparent from the following detailed description of a several embodiments which proceeds with reference to the accompanying figures.

BRIEF DESCRIPTION OF THE DRAWINGS

FIGS. 2A-2B are digital images and graphs showing the effect of antibiotic treatment on wound healing in mice. FIG. 2A Antibiotic ointment or petrolatum was administered daily to the right or left dorsum of individual mice (side selected at random). The contralateral side remained untreated. FIG. 2B Mice were injected with antibiotics daily. Six mm excisional biopsies were taken from the right and left dorsum of each animal. The left panels show representative photographs of biopsy sites over time. Wound size was recorded by digital photography. The mean rate of wound repair was calculated based on the original wound area of each biopsy site. The percent repair over time (mean±SE of all sites, N=10/treatment group) is shown. **p<0.001 vs untreated wound sites.

FIG. 3 is a set of digital images and graphs showing the effect of CpG and/or IMQ on wound healing in mice treated with antibiotic ointment. Six mm excisional biopsies were taken from the right and left dorsum of individual mice. One biopsy site (selected at random) was treated on days 0, 2 and 4 with antibiotic while the other was treated with antibiotic+ 50 ug CpG ODN and/or 5 ug IMQ. The percent repair over time (mean±SE of all sites, n=5/treatment group) is shown. **p<0.001 vs antibiotic treated sites.

FIG. 7 is a bar graph of the effect of antibiotic ointment on the expression of TLR7 and TLR9. Total RNA was extracted from the skin after 14 days of treatment with antibiotic ointment. Quantitative RT-PCR was performed to detect TLR7 and TLR9. Results represent the mean±SE of at least 4 independent samples/treatment group. No significant difference was noted.

SEQUENCES

Sequence Listing

Figure 1:
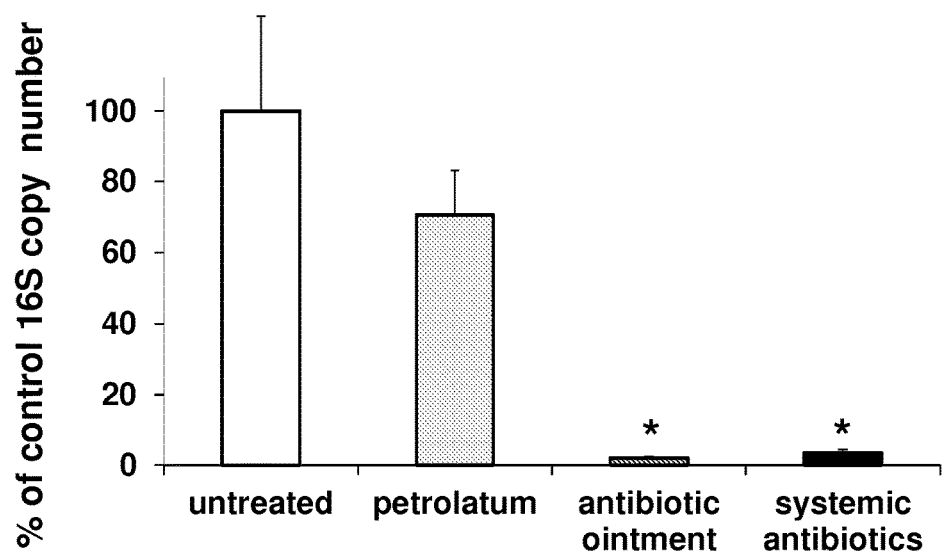
FIG. 1 is a bar graph of a quantitative analysis of bacterial DNA on skin. Mice were injected with antibiotics (systemic) or treated topically with antibiotic ointment or petrolatum. Genomic bacterial DNA was isolated from swabbed skin samples and the amount of 16S rRNA determined by QT-PCR. Results represent the mean±SE of 3 independent samples/treatment group. *p<0.05.

The Sequence Listing is submitted as an ASCII text file [4239-88072-05_Sequence_Lisitng.txt, Oct. 23, 2014, 8.84 KB], which is incorporated by reference herein.

The nucleic and amino acid sequences listed are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

DETAILED DESCRIPTION

Antibiotic treatment eliminates bacteria from the skin, but delays wound healing. It is disclosed herein that this adverse consequence of antibiotics is corrected by co-administering a K-type CpG ODN and an imidazoquinoline having toll-like receptor 7 (TLR7) ligand, such as imiquimod or resiquimod. Pharmaceutical compositions including these agents are provided. The pharmaceutical compositions are formulated for topical administration, such as to the skin or the eye.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Amplification: Of a nucleic acid molecule (such as a DNA or RNA molecule) refers to use of a technique that increases the number of copies of a nucleic acid molecule in a specimen. An example of amplification is the polymerase chain reaction, in which a biological sample collected from a subject is contacted with a pair of oligodeoxynucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of amplification may be characterized by electrophoresis, restriction endonuclease cleavage patterns, oligodeoxynucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134. Amplification reactions can be used to produce CpG ODN.

Animal: Living multi-cellular vertebrate organisms, a category that includes, for example, mammals and birds. The term mammal includes both human and non-human mammals. Similarly, the term "subject" includes both human and veterinary subjects.

Antibiotic: A compound or substance that kills or substantially slows down the growth of bacteria, fungus or any other microbe. An "antibacterial" is a compound or substance that kills or substantially slows the growth of bacteria.

Antibacterial antibiotics are commonly classified based on their mechanism of action, chemical structure, or spectrum of activity. Most target bacterial functions or growth processes. Those that target the bacterial cell wall (for example, penicillins and cephalosporins) or the cell membrane (for example, polymixins), or interfere with essential bacterial enzymes (for example, quinolones and sulfonamides) are bactericidal. Those that target protein synthesis (for example, aminoglycosides, macrolides, and tetracyclines) are generally bacteriostatic. Further categorization is based on their target specificity.

"Narrow-spectrum" antibacterial antibiotics target specific types of bacteria, such as Gram-negative or Gram-positive bacteria. "Broad-spectrum antibiotics" affect a number of different types of bacteria. Antibacterial agents also include cyclic lipopeptides (such as daptomycin), glycylcyclines (such as tigecycline), and oxazolidinones (such as linezolid).

Topical antibiotics are antibiotics that are applied to a body surface, such as the skin or eye. Topical antibiotics are often formulated in an ointment or a cream, and contain active agents such as macrolide antibiotic (such as erythromycin), a sulfa antibiotic (such as sulfacetamide), a cyclic peptide (such as bacitracin a polymyxin) a psuedomonic acid (such as mupirocin), an ammyroglycoside (such as neomycin), or a quinolone (such as ciprofloxacin or ofloxacin), a nitroimidazole (such as metronidazloe), or a combination of drugs (such as bacitracine/polymyxin or neomycin/polymyxin B/bacitracin).

Basal Membrane and Basal Membrane extract: Basement membranes are sheets of extracellular matrix found at the base of all lumen-lining epithelial and endothelial cells. They are generally comprised of basement membrane proteins, including collagen IV, laminin I, heparan sulfate proteoglycan and entactin. Basement Membrane Extract can be used for promotion and maintenance of a differentiated phenotype in a variety of cell cultures including primary epithelial cells, endothelial cells, and smooth muscle cells. It has been employed in angiogenesis assays, tumor cell invasion assays, and as a vehicle to augment the tumorigenicity of injected tumor cells in nude mice. BME is available commercially as MATRIGEL® and CULTREX®, amongst others. One known basement membrane complex, is disclosed in U.S. Pat. No. 4,829,000 to Kleinman et al., and is commercially available as MATRIGEL®, from BD Biosciences of San Jose, Calif. Membrane components extracted from a spontaneous mouse tumor, the Engelbreth-Holm-Swarm (EHS) tumor have been used for studying both two dimensional and three dimensional cell-matrix interactions. It is used routinely in labs throughout the world for studies of basement membrane-cell interactions, angiogenesis (in vitro and in vivo), tumor invasion, and as a scaffold for tissue engineering applications. Another method, as taught in U.S. Pat. No. 5,147,782 to Brocks et al., extracts basement membrane components from human and animal tissues in the presence of a chelating agent. Synthetic matrices are also commercially available, such as PURAMATRIX™ from BD Biosciences and CYTOMATRIX™, from Cytomatrix, LLC.

CpG or CpG motif: A nucleic acid having a cytosine followed by a guanine linked by a phosphate bond in which the pyrimidine ring of the cytosine is unmethylated. The term "methylated CpG" refers to the methylation of the cytosine on the pyrimidine ring, usually occurring at the 5-position of the pyrimidine ring. A CpG oligodeoxynucleotide is an oligodeoxynucleotide that is at least about ten nucleotides in length and includes an unmethylated CpG. CpG oligodeoxynucleotides include both D and K-type oligodeoxynucleotides (see below). CpG oligodeoxynucleotides are single-stranded. The entire CpG oligodeoxynucleotide can be unmethylated or portions may be unmethylated. In one embodiment, at least the C of the 5' CG 3' is unmethylated.

D-type Oligodeoxynucleotide (D ODN): A D-type ODN is at least about 16 nucleotides in length, such as 16 to 30 nucleotides in length, and includes a sequence represented by the following formula:

(SEQ ID NO: 1)
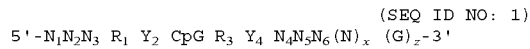

wherein the central CpG motif is unmethylated, R is a purine nucleotide, Y is a pyrimidine nucleotide, N is any nucleotide, X is any integer from 0 to 10, and Z is any integer from 4 to 10. Additional detailed description of D ODN sequences and their activities can be found in Verthelyi et al., *J. Immunol.* 166:2372-2377, 2001, which is herein incorporated by reference. Generally D ODNs can stimulate a cellular immune response.

Epithelial Cell: A closely packed cell that forms an epithelium, such as in the skin. There are several types of epithelium, including simple squamous epithelium, simple cuboidal epithelium, simple columnar epithelium, pseudostratified columnar epithelium, stratified squamous (nonkeratinized) epithelium, stratified cuboidal epithelium, and transitional epithelium.

Imiquimod: A compound, 3-(2-methylpropyl)-3,5,8-triazatricyclo[7.4.0.0$^{2,6}$] trideca-1(9),2(6),4,7,10,12-hexaen-7-amine, also known as R-837, 1-isobutyl-1H-imidazo[4,5-c]quinolin-4-amine, or ALDARA® The original FDA approval for imiquimod was on Feb. 27, 1997, FDA Application No. (NDA) 020723. Imiquimod is approved to treat actinic keratosis, superficial basal cell carcinoma, and external genital warts. Imiquimod activates immune cells through the toll-like receptor 7 (TLR7), commonly involved in pathogen recognition. Cells activated by imiquimod via TLR-7 secrete cytokines (primarily interferon-α (IFN-α), interleukin-6 (IL-6) and tumor necrosis factor-α (TNF-α)). Imiquimod has the structure:

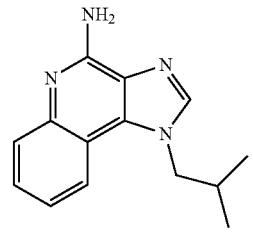 [SMILES: CC(C)Cn1cnc2c(N)nc3ccccc3c21]

Isolated: An "isolated" nucleic acid has been substantially separated or purified away from other nucleic acid sequences in the cell of the organism in which the nucleic acid naturally occurs, i.e., other chromosomal and extrachromosomal DNA and RNA. The term "isolated" thus encompasses nucleic acids purified by standard nucleic acid purification methods. The term also embraces nucleic acids prepared by recombinant expression in a host cell as well as chemically synthesized nucleic acids.

K-type CpG Oligodeoxynucleotide (K ODN): An oligodeoxynucleotide including an unmethylated CpG motif that has a sequence represented by the formula:

(SEQ ID NO: 2)
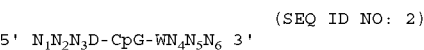

wherein the central CpG motif is unmethylated, D is T, G or A, W is A or T, and $N_1$, $N_2$, $N_3$, $N_4$, $N_5$, and $N_6$ are any nucleotides. In one embodiment, D is a T. Additional detailed description of K ODN sequences and their activities can be found in the description below. Generally K ODNs can stimulate a humoral response. For example, K ODNs stimulate the production of immunoglobulins, such as IgM and IgG. K ODNs can also stimulate proliferation of peripheral blood mononuclear cells and increase expression of IL-6 and/or IL-12, amongst other activities. In several embodiments, K ODNs are about 10 to about 30 nucleotides in length.

Mammal: This term includes both human and non-human mammals. Similarly, the term "subject" includes both human and veterinary subjects.

Nucleic acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Oligonucleotide: A linear polynucleotide sequence of up to about 200 nucleotide bases in length, for example a polynucleotide (such as DNA, oligodeoxynucleotides or RNA, oligoribonucleotides) which is at least six nucleotides, for example at least 10, 15, 50, 100 or even 200 nucleotides long.

A "stabilized oligonucleotide" is an oligonucleotide that is relatively resistant to in vivo degradation (for example via an exo- or endo-nuclease). In one embodiment, a stabilized oligonucleotide has a modified phosphate backbone. One specific, non-limiting example of a stabilized oligonucleotide has a phophorothioate modified phosphate backbone (wherein at least one of the phosphate oxygens is replaced by sulfur). Other stabilized oligonucleotides include: non-ionic DNA analogs, such as alkyl- and aryl-phosphonates (in which the charged phosphonate oxygen is replaced by an alkyl or aryl group), phophodiester and alkylphosphotriesters, in which the charged oxygen moiety is alkylated. Oligonucleotides which contain a diol, such as tetraethyleneglycol or hexaethyleneglycol, at either or both termini have also been shown to be substantially resistant to nuclease degradation.

An "immunostimulatory oligonucleotide," "immunostimulatory CpG containing oligodeoxynucleotide," "CpG ODN," refers to an oligodeoxynucleotide, which contains a cytosine, guanine dinucleotide sequence. In one embodiment, CpG ODN stimulates (e.g. has a mitogenic effect or induces cytokine production) vertebrate immune cells. CpG ODN can also stimulate angiogenesis. The cytosine, guanine is unmethylated. This includes K and D ODN.

An "oligonucleotide delivery complex" is an oligonucleotide associated with (e.g. ionically or covalently bound to; or encapsulated within) a targeting means (e.g. a molecule that results in a higher affinity binding to a target cell (e.g. B cell or natural killer (NK) cell) surface and/or increased cellular uptake by target cells). Examples of oligonucleotide delivery complexes include oligonucleotides associated with: a sterol (e.g. cholesterol), a lipid (e.g. cationic lipid, virosome or liposome), or a target cell specific binding agent (e.g. a ligand recognized by a target cell specific receptor). Generally, the complexes must be sufficiently stable in vivo to prevent significant uncoupling prior to internalization by the target cell. However, the complex should be cleavable or otherwise accessible under appropriate conditions within the cell so that the oligonucleotide is functional. (Gursel, *J. Immunol.* 167:3324, 2001)

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence, if the promoter affects the transcription or expression of the coding sequence. Generally, operably linked DNA sequences are contiguous and, where necessary to join two protein coding regions, in the same reading frame.

Pharmaceutical agent or drug: A chemical compound, nucleic acid molecule, or composition capable of inducing a desired therapeutic or prophylactic effect when properly administered to a subject. In one embodiment, a pharmaceutical agent induces angiogenesis or the production of VEGF.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the oligodeoxynucleotides herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. Acceptable carriers also include creams and ointments, such as for topical administration.

Polynucleotide: A linear nucleic acid sequence of any length. Therefore, a polynucleotide includes molecules which are 10, 15, 50, 100, 200 (oligonucleotides) and also nucleotides as long as a full length cDNA.

Purified: The term purified does not require absolute purity; rather, it is intended as a relative term. Thus, for example, a purified oligonucleotide preparation is one in which the oligodeoxynucleotide is more enriched than the protein is in its generative environment, for instance within a cell or in a biochemical reaction chamber. Preferably, a preparation of oligodeoxynucleotide is purified such that the oligodeoxynucleotide represents at least 50% of the total nucleotide content of the preparation.

Resiquimod: A drug, also known as R-848 or 1-[4-amino-2-(ethoxymethyl) imidazo[4,5-c]quinolin-1-yl]-2-methylpropan-2-ol, that acts as an immune response modifier. It is used as a topical cream in the treatment of skin lesions such as those caused by herpes simplex virus. It has also been used as an adjuvant to increase the effectiveness of vaccines. It is an agonist for toll-like receptor 7 and 8 and an upregulator of the opioid growth factor receptor. Resiquimod has the structure:

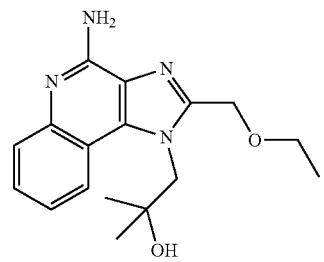 [SMILES: CCOCc1nc2c(N)nc3ccccc3c2n1CC(C)(C)O]

Surfactant: A compound that lowers the surface tension of a liquid, the interfacial tension between two liquids, or that between a liquid and a solid. Surfactants may act as detergents, wetting agents, emulsifiers, foaming agents, and dispersants. Polysorbates are a class of emulsifiers. Polysorbates are oily liquids derived from PEG-ylated sorbitan (a derivative of sorbitol) esterified with fatty acids. Polysorbate 20 (Polyoxyethylene (20) sorbitan monolaurate; commercial brand names include TWEEN® 20) is a polysorbate surfactant whose stability and relative non-toxicity allows it to be used as a detergent and emulsifier in a number of pharmacological applications. It is a polyoxyethylene derivative of sorbitan monolaurate, and is distinguished from the other members in the polysorbate range by the length of the polyoxyethylene chain and the fatty acid ester moiety. Polysorbae 40 (Polyoxyethylene (20) sorbitan monopalmitate), Polysorbate 60 (Polyoxyethylene (20) sorbitan monostearate) and Polysorbate 80 (Polyoxyethylene (20) sorbitan monooleate) can also be used in the methods disclosed herein.

Therapeutically effective dose: A dose sufficient to induce epithelial growth, or promote wound healing. In one embodiment, a therapeutically effective dose is an amount sufficient to produce increased division or survival of epithelial cells or is sufficient to promote survival of a graft in a subject.

Toll-like Receptors (TLR): Conserved molecular receptors that recognize bacterial, fungal, protozoal and viral components. In humans, at least ten known TLRs are known to recognize different pathogenic molecular markers, such as viral double-stranded RNA (TLR3), flagellin (TLR5) and components of bacterial cell wall including lipopolysaccharide (LPS; TLR4) or lipopeptide (TLR2). Ligand-stimulated TLRs interact with various Toll/interleukin-1 receptor (TIR) domain. Thirteen TLRs (TLR1 to TLR13) have been identified in humans and mice together, and equivalent forms of many of these have been found in other mammalian species.

TLRs recognize conserved motifs found in various pathogens and mediate defense responses. Triggering of the TLR pathway leads to the activation of NF-κB and subsequent regulation of immune and inflammatory genes. The TLRs and members of the interleukin (IL)-1 receptor family share a conserved stretch of about 200 amino acids known as the TIR domain. Upon activation, TLRs associate with a number of cytoplasmic adaptor proteins containing TIR domains including MyD88 (myeloid differentiation factor), MAL/TIRAP (MyD88-adaptor-like/TIR-associated protein), TRIF (Toll-receptor-associated activator of interferon) and TRAM (Toll-receptor associated molecule). Cells in vivo, express TLRs as 4- and 6-kb transcripts that are most abundant in placenta and pancreas. TLR activity includes activation of NF-κB. Activation of TLRs can result in increased production of tumor necrosis factor α (TNFα), interleukin (IL)-1β, IL-6, IL-8, IL-12, RANTES, MIP-1α, and MIP-1β.

TLR7 interacts with single- and double-stranded RNA in a sequence-dependent manner, as well as with the imidazoquinolines imiquimod (R837) and resiquimod (R848). In humans, TLR7 is expressed in B cells and both myeloid dendritic cells (mDC) and plasmacytoid dendritic cells (pDC). In mice, TLR7 is expressed in pDC. TLR8 interacts with single-stranded RNA in a sequence-dependent manner, as well as with the imidazoquinolines imiquimod (R837) and resiquimod (R848) (see, Heil F et al. (2004) Science 303:1526-9). In humans, TLR8 is expressed in myeloid cells, but TLR8 is not expressed in mice.

TLR9 interacts with DNA containing CpG motifs that include unmethylated 5' cytosine-guanine 3' (CG) dinucleotides occurring within the context of certain short flanking nucleotide sequences. Hemmi H et al. (2000) Nature 408: 740-5. In humans TLR9 is expressed in B cells and pDC. In mice, TLR9 is expressed in B cells, pDC, and mDC.

Topical application: A topically applied agent is applied only in a specific area, and not throughout the body. In particular examples the composition is applied to the skin or the eye in an area where re-epithelialzation is desired. For example the pharmaceutical composition can be applied in a topical preparation to a wound, such as an epithelial wound or defect, for example a traumatic or surgical wound, such as a skin or corneal abrasion or surgical incision.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Pharmaceutical Compositions

The compositions disclosed herein comprise an effective amount of 1) an imidazoquinoline having toll-like receptor 7 (TLR7) ligand activity, 2) an immunostimulatory K-type CpG oligodeoxynucleotide (ODN) comprising an unmethylated CpG motif, 3) an antibiotic, and 4) a surfactant, wherein the composition is formulated for topical administration. Antibiotic treatment eliminates bacteria from the skin, but delays wound healing. The present compositions eliminate bacteria but do not delay healing of a wound.

While many effective formulations are provided herein, exemplary non-limiting formulations (volume (v)/v) includes a ratio about 4 to about 6% (v/v) of a surfactant, about 80 to about 90% of an antibacterial ointment, and about 16% to about 4% of a solution of a Toll-like receptor ligand and a CpG oligodoexynucleotide (ODN). In one non-limiting example, the composition includes about 4 to about 6% of a surfactant, such as a polysorbate, about 82% to about 87% of a liquefied antibacterial ointment, and about 14% to about 7% of a solution of a Toll-like receptor ligand and a CpG oligodoexynucleotide (ODN). In a further non-liming example, the composition includes about 4% to about 6% of a surfactant, about 86% to about 84% of a liquefied antibiotic ointment, and about 10% TLR ligand/CpG ODN (v/v). In a further non-liming example, the composition includes about 5% polysorbate: 85% liquefied antibacterial ointment: 10% TLR ligand/CpG ODN (v/v). Each of the components in these compositions is described in detail below. For each of these embodiments, it is understood that any K-type ODN (such as but not limited to, those including the nucleic acid sequences set forth as SEQ ID NOs: 2-33, and combinations thereof). In addition, either resiquimod or imiquimod can be included in the composition. Furthermore, antibiotics of use in all of these formulations are disclosed. Surfactants of use are also disclosed below, and include, but are not limited to polysorbate 20, polysorbate 40, polysorbate 60 and polysorbate 80. Any of the compositions disclosed herein are of use to treat wounds, since they are bactericidal and accelerate healing of the wound.

K-Type CpG ODN

The present pharmaceutical compositions include a therapeutically effective amount of a K-type CpG oligodeoxynucleotide (ODN). A CpG oligodeoxynucleotide is an oligodeoxynucleotide including a CpG motif, wherein the pyrimdine ring of the cytosine is unmethylated. Two types of CpG ODNs have been identified: K-type and D-type ODNs. In several embodiments, the CpG ODN is at most 100 nucleotides or at most 80 nucleotides in length. In other embodiments the CpG ODN is in the range of about 8 to 30 nucleotides in length. In another embodiment, the CpG ODN is at least 10 nucleotides in length, such as about 10 to about 30 nucleotides in length.

K-type nucleic acids sequences of use are described in the published PCT Applications No. WO 98/18810A1 (K-type), which is incorporated by reference herein in their entirety. Generally, only K-type CpG ODNs are used in the methods disclosed herein. Thus, in several embodiments, the methods do not include the use of D-type ODNs. Combinations of K-type CpG ODNs are of use, such as the use of at least two, at least three, at least four, at least five, at least six at least seven, at least eight or at least ten ODNs, each with a different nucleic acid sequence. In several embodiments, two, three, four, five or six K-type CpG ODNs, each with a different nucleic acid sequence, are utilized in the methods.

A single K ODN can be used in the methods disclosed herein, or mixtures of K ODN can also be used in the methods disclosed herein. Specific combinations of ODNs are disclosed, for example, in U.S. patent application Ser. No. 10/194,035, which is incorporated herein by reference.

In several embodiments, a K-type CpG ODN or a mixture of K-type CpG ODNs is utilized. Briefly, the K-type nucleic acid sequences useful in the methods disclosed herein are represented by the formula:

5'-N₁DCGYN₂-3' wherein at least one nucleotide separates consecutive CpGs; D is adenine, guanine, or thymidine; Y is cytosine or thymine, N is any nucleotide and $N_1+N_2$ is from about 0-26 bases. In one embodiment, $N_1$ and $N_2$ do not contain a CCGG quadmer or more than one CGG trimer; and the nucleic acid sequence is from about 8-30 bases in length, such as about 10 to 30 nucleotides in length. However, nucleic acids of any size (even many kb long) can be used in the methods disclosed herein if CpGs are present. In one embodiment, synthetic oligonucleotides of use do not include a CCGG quadmer or more than one CCG or CGG trimer at or near the 5' or 3' terminals and/or the consensus mitogenic CpG motif is not a palindrome. A "palindromic sequence" or "palindrome" means an inverted repeat (i.e., a sequence such as ABCDEE'D'C'B'A', in which A and A' are bases capable of forming the usual Watson-Crick base pairs).

In another embodiment, the methods include the use of an oligodeoxynucleotide which contains a CpG motif represented by the formula:

5'-N₁RDCGYTN₂-3' wherein at least one nucleotide separates consecutive CpGs; RD is selected from the group consisting of GpT, GpG, GpA, ApT and ApA; YT is selected from the group consisting of TpT or CpT; N is any nucleotide and $N_1+N_2$ is from about 0-26 bases, such that the ODN is about 8 to 30 nucleotides in length.

In several embodiments, the methods disclosed herein include the use of an effective amount of at least one K-type CpG ODN, wherein the K-type CpG ODN includes an unmethylated CpG motif that has a sequence represented by the formula:

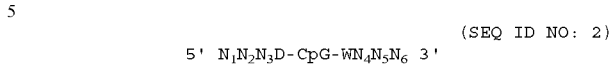

(SEQ ID NO: 2)
5' N₁N₂N₃D-CpG-WN₄N₅N₆ 3' wherein the central CpG motif is unmethylated, D is T, G or A, W is A or T, and $N_1$, $N_2$, $N_3$, $N_4$, $N_5$, and $N_6$ are any nucleotides. In one embodiment, D is a T. The K ODN(s) can be 10 to 30 nucleotides in length. A K-type CpG ODN can include multiple CpG motifs. In some embodiments, at least one nucleotide separates consecutive CpGs; N₃D is selected from the group consisting of GpT, GpG, GpA, ApT and ApA; WN₄ is selected from the group consisting of TpT or CpT; N is any nucleotide and $N_1+N_2$ is from about 0-26 bases In one embodiment, $N_1$, and $N_2$ do not contain a CCGG quadmer or more than one CCG or CGG trimer. CpG ODN are also in the range of 8 to 30 bases in length, but may be of any size (even many kb long) if sufficient motifs are present. In several examples, the CpG ODN is 10 to 20 nucleotides in length, such as 12 to 18 nucleotides in length. In one embodiment, synthetic oligodeoxynucleotides of this formula do not include a CCGG quadmer or more than one CCG or CGG trimer at or near the 5' and/or 3' terminals and/or the consensus CpG motif is not a palindrome. Other CpG oligodeoxynucleotides can be assayed for efficacy using methods described herein. It should be noted that exemplary K-type CpG ODNs are known in the art, and have been fully described, for example in PCT Publication No. WO 98/18810A1, which is incorporated herein by reference.

Exemplary K-type CpG ODN of use individually, and in any combination, are listed below:

K ODN
KX
                          (SEQ ID NO: 3)
ATAATCGACGTTCAAGCAAG

K22
                          (SEQ ID NO: 4)
CTCGAGCGTTCTC

K21
                          (SEQ ID NO: 5)
TCTCGAGCGTTCTC

K82
                          (SEQ ID NO: 6)
ACTCTGGAGCGTTCTC

K30
                          (SEQ ID NO: 7)
TGCAGCGTTCTC k31
                          (SEQ ID NO: 8)
TCGAGGCTTCTC

K39
                          (SEQ ID NO: 9)
GTCGGCGTTGAC

K16
                          (SEQ ID NO: 10)
TCGACTCTCGAGCGTTCTC

K3
                          (SEQ ID NO: 11)
ATCGACTCTCGAGCGTTCTC k23 (SEQ ID NO: 12)
TCGAGCGTTCTC

K40 (SEQ ID NO: 13)
GTCGGCGTCGAC

K34 (SEQ ID NO: 14)
GTCGACGTTGAC

K83 (SEQ ID NO: 15)
ACTCTCGAGGGTTCTC

K19 (SEQ ID NO: 16)
ACTCTCGAGCGTTCTC

K73 (SEQ ID NO: 17)
GTCGTCGATGAC

K46 (SEQ ID NO: 18)
GTCGACGCTGAC

K47 (SEQ ID NO: 19)
GTCGACGTCGAC

K72 (SEQ ID NO: 20)
GTCATCGATGCA

K37 (SEQ ID NO: 21)
GTCAGCGTCGAC k25 (SEQ ID NO: 22)
TCGAGCGTTCT

K82 (SEQ ID NO: 23)
ACTCTGGAGCGTTCTC

K83 (SEQ ID NO: 24)
ACTCTCGAGGGTTCTC

K84 (SEQ ID NO: 25)
ACTCTCGAGCGTTCTA

K85 (SEQ ID NO: 26)
CATCTCGAGCGTTCTC

K89 (SEQ ID NO: 27)
ACTCTTTCGTTCTC

K109 (SEQ ID NO: 28)
TCGAGCGTTCT

K123 (SEQ ID NO: 29)
TCGTTCGTTCTC

K1555 (SEQ ID NO: 30)
GCTAGACGTTAGCGT

K110 (SEQ ID NO: 31)
TCGAGGCTTCTC

CpG10103 (SEQ ID NO: 32)
TCGTCGTTTTCGGTCGTTTT

CpG 7909 (SEQ ID NO: 33)
TCGTCGTTTTGTCGTTTTGTCGTT

Exemplary Control ODNs are:

K1612 (SEQ ID NO: 34)
TAGAGCTTAGCTTGC

C163 (SEQ ID NO: 35)
TTGAGTGTTCTC

As noted above, combinations of K-type CpG ODN can also be used. Exemplary combinations include 1) K3, K19, K110; 2) K19, K23, K123; K3, 3) K110, K123; 4) K3, K23, K123; 5) K3, K19, K123; and 6) K19, K110, K123. Additional exemplar combinations include at least two different K-type CpG ODNS, wherein one of the K-type CpG ODNs is K1555, and/or wherein one of the K-type CpG ODNs is K3.

For use in the methods disclosed herein, ODNs can be synthesized de novo using any of a number of procedures well known in the art. For example, the b-cyanoethylphosphoramidite method (Beaucage et al., *Tet. Let.* 22:1859, 1981) or the nucleoside H-phosphonate method (Garegg et al., *Tet. Let.* 27:4051, 1986; Froehler et. al., *Nucl. Acid Res.* 14:5399, 1986; Garegg et al., *Tet. Let.* 27:4055, 1986; Gaffney et al., *Tet. Let.* 29:2619, 1988) can be utilized. These chemistries can be performed by a variety of automated oligonucleotide synthesizers available in the market.

Alternatively, CpG dinucleotides can be produced on a large scale in plasmids, (see Sambrook, et al., *Molecular Cloning: A Laboratory Manual*, Cold Spring Harbor Laboratory Press, New York, 1989) which after being administered to a subject are degraded into oligonucleotides. Oligonucleotides can be prepared from existing nucleic acid sequences (e.g., genomic or cDNA) using known techniques, such as those employing restriction enzymes, exonucleases or endonucleases (see PCT Application No. PCT/US98/03678).

For use in vivo, nucleic acids can be utilized that are relatively resistant to degradation (such as by endo- and exo-nucleases). Secondary structures, such as stem loops, can stabilize nucleic acids against degradation. Alternatively, nucleic acid stabilization can be accomplished via phosphate backbone modifications. In one embodiment, a stabilized nucleic acid has at least a partial phosphorothioate modified backbone. Phosphorothioates may be synthesized using automated techniques employing either phosphoramidate or H-phosphonate chemistries. Aryl- and alkyl-phosphonates can be made (e.g., as described in U.S. Pat. No. 4,469,863) and alkylphosphotriesters (in which the charged oxygen moiety isalkylated, as described in U.S. Pat. No. 5,023,243 and European Patent No. 092,574), and can be prepared by automated solid phase synthesis using commercially available reagents.

In one embodiment, the phosphate backbone modification occurs at the 5' end of the nucleic acid. One specific, non-limiting example of a phosphate backbone modification is at the first two nucleotides of the 5' end of the nucleic acid. In another embodiment, the phosphate backbone modification occurs at the 3' end of the nucleic acid. One specific, non-limiting example of a phosphate backbone modification is at the last five nucleotides of the 3' end of the nucleic acid.

Methods for making other DNA backbone modifications and substitutions have been described (Uhlmann et al., *Chem. Rev.* 90:544, 1990; Goodchild, *Bioconjugate Chem.* 1:1, 1990). 2'-O-methyl nucleic acids with CpG motifs also cause angiogenesis, as do ethoxy-modified CpG nucleic acids. In fact, no backbone modifications have been found that completely abolish the CpG effect, although it is greatly reduced by replacing the C with a 5-methyl C.

For administration in vivo, nucleic acids may be associated with a molecule that results in higher affinity binding to target cell (such as an epithelial cell) surfaces and/or increased cellular uptake by target cells to form a "nucleic acid delivery complex." Nucleic acids can be ionically or covalently associated with appropriate molecules using techniques which are well known in the art (see below). Nucleic acids can alternatively be encapsulated in liposomes or virosomes using well-known techniques.

A K-type CpG ODN can be associated with (for example, ionically or covalently bound to, or encapsulated within) a targeting moiety. Targeting moieties include any a molecule that results in higher affinity binding to a target cell, such as, but not limited to, an endothelial cell.

A variety of coupling or cross-linking agents can be used to form the delivery complex, such as protein A, carbodiamide, and N-succinimidyl (2-pyridyldithio) propionate (SPDP). Examples of delivery complexes include K-type CpG ODNs associated with a sterol (such as cholesterol), a lipid (such as a cationic lipid, virosome or liposome), and a target cell specific binding agent (such as a ligand recognized by target cell specific receptor). In one embodiment, the complexes are sufficiently stable in vivo to prevent significant uncoupling prior to internalization by the target cell. However, these complexes can be cleavable under appropriate circumstances such that the oligodeoxynucleotide can be released in a functional form (see, for example, PCT Application No. WO 00/61151).

A therapeutically effective amount of at least one K-type ODN is included in the disclosed pharmaceutical compositions. Suitable concentrations include, but are not limited to, about 100 to about 1,000 µg/gm K-type ODN, such as about 200 to about 800 µg/gm, such as about 300 to 700 µg/gm, such as about 500 µg/gm K-type CpG ODN.

Antibiotics

Antibiotics (antibacterial agents) are compounds that kill or slows down the growth of bacteria. The successful outcome of antimicrobial therapy with antibacterial compounds depends on several factors. These include host defense mechanisms, the location of infection, and the pharmacokinetic and pharmacodynamic properties of the antibiotic. A variety of antibiotics are known, including those that target the bacterial cell wall (for example, penicillins and cephalosporins) or the cell membrane (for example, polymixins), or interfere with essential bacterial enzymes (for example, quinolones and sulfonamides). Antibiotics include, but are not limited to, clindamycin, erythromycin, tetracycline, minocycline, doxycycline, penicillin, ampicillin, carbenicillin, methicillin, cephalosporins, vancomycin, and bacitracin, streptomycin, gentamycin, chloramphenicol, fusidic acid, ciprofloxin and other quinolones, sulfonamides, trimethoprim, dapsone, isoniazid, teicoplanin, avoparcin, synercid, virginiamycin, cefotaxime, ceftriaxone, piperacillin, ticarcillin, cefepime, cefpirome, rifampicin, pyrazinamide, ciprofloxacin, levofloxacin, enrofloxacin, amikacin, netilmycin, imipenem, meropenem, inezolid, pharmaceutically acceptable salts thereof, and prodrugs thereof. Generally, the antibiotics of use in the methods disclosed herein are formulated for topical administration.

Polymyxin is a generic term for a group of closely related antibiotic substances that disrupt the structure of the bacterial cell membrane by interacting with phospholipids. Polymixins are produced by the Gram-positive bacterium *Bacillus polymyxa* and are selectively toxic for Gram-negative bacteria due to their specificity for the lipopolysaccharide molecule that exists within many Gram-negative outer membranes.

Polymyxin B is the least toxic of these and is generally available for clinical use. The activity of Polymyxin B is restricted to gram-negative bacteria. A concentration of about 0.1 to about 0.25% in aqueous solution is non-irritating and effective. Polymyxin B has the structure:

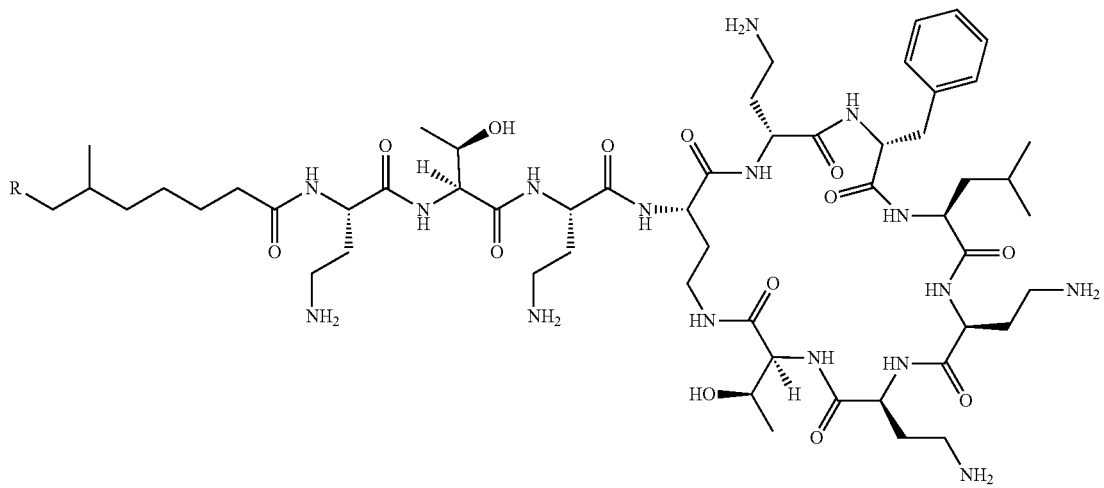

Generally, the aminoglycoside class of antibiotics contains two or more aminosugars connected by glycosidic bonds. Neamine (two rings), Ribostamycin (three rings), Paromomycin (four rings), and Lividomycin (five rings) are some other examples of aminoglycosides. Neomycin is an aminoglycoside antibiotic that is a complex of three compounds, Neomycins A, B & C. Commercial preparations are usually made with Neomycin B, which is a water soluble, thermostable substance. The sulfate complex is stable in the dry state, or in solution, at room temperature. It is a broad spectrum antibiotic, commonly marketed in dermatological and ophthalmic ointments, or as a sterile powder for dilution with saline solution for topical application or parenteral injection. Neomycin B has the structure:

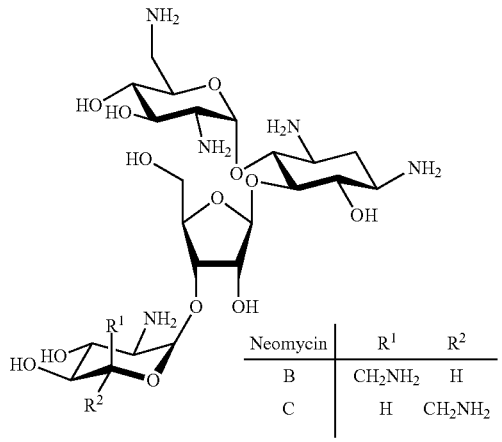

| Neomycin | $R^1$ | $R^2$ |
|---|---|---|
| B | $CH_2NH_2$ | H |
| C | H | $CH_2NH_2$ |

Bacitracin is a mixture of related cyclic polypeptides produced by organisms of the licheniformis group of *Bacillus subtilis* var Tracy that acts on Gram-positive cell walls. It has the structure:

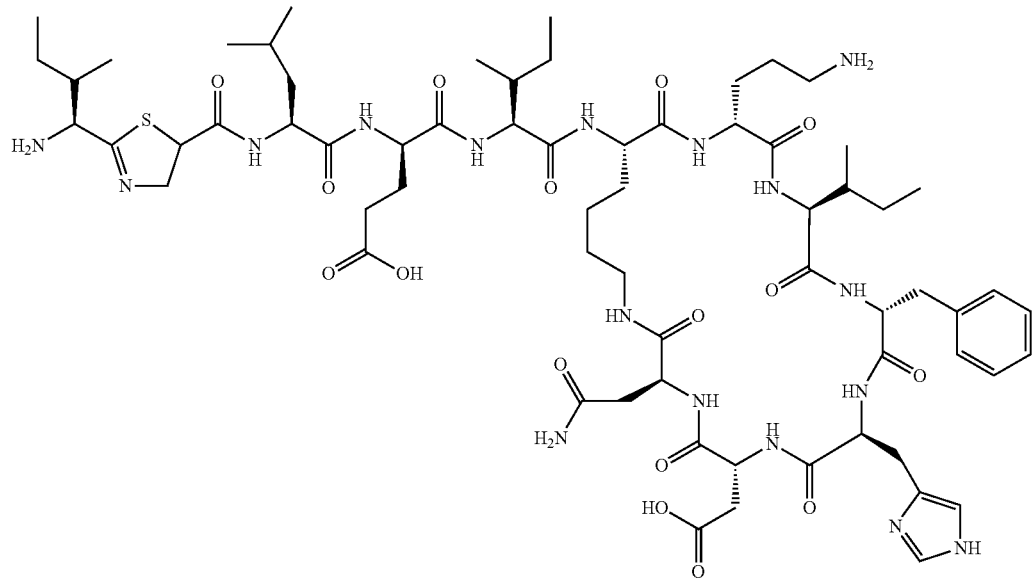 [SMILES: CCC(C)[C@H](N)C1=NCC(C(=O)N[C@@H](CC(C)C)C(=O)N[C@H](CCC(=O)O)C(=O)N[C@H](C(=O)N[C@H]2CCCCNC(=O)[C@H](CC(N)=O)NC(=O)[C@@H](CC(=O)O)NC(=O)[C@H](Cc3c[nH]cn3)NC(=O)[C@@H](Cc3ccccc3)NC(=O)[C@H](C(C)CC)NC(=O)[C@@H](CCCN)NC2=O)C(C)CC)S1]

Several topical antibiotic formulations are known that employ Polymyxin B sulfate in a suspension in combination with Neomycin Sulfate. Some such formulations include additional active ingredients, such a lidocaine hydrochloride and/or zinc Bacitracin. These products are generally available in an oil base, such as in petrolatum, mineral oil, emulsifying wax, or a combination of those substances. Some examples of commercially sold formulations include the following:

NEOSPORIN™ ointment: Polymyxin B Sulfate, Neomycin, Zinc Bacitracin, and Lidocaine, in emulsifying wax, mineral oil, purified water, and white petrolatum.

CAMPHO-PHENIQUE™ Triple Antibiotic Ointment Plus Pain Reliever: containing Zinc Bacitracin, Neomycin Sulfate, Polymyxin B Sulfate, and Lidocaine in a white petrolatum base.

MYCATRACIN™ Triple Antibiotic First Aid Ointment: Bacitracin, Neomycin Sulfate, Polymyxin B Sulfate in a microcrystalline wax, mineral oil and white petrolatum base. Micatrin™ Plus Pain Reliever also contains Lidocaine.

Exemplary amounts of antibiotics are Polymyxin B Sulfate (about 5,000- about 10,000 units/gm) Neomycin Sulfate (about 1.75- about 3.5 mg/gm). Other antibiotics include Gramicidin (about 0.025 mg/gm), Zinc Bacitracin (about 400-about 500 units/gm), Gentamicin (about 0.3%); Chloramphenicol (about 0.5%), Tobramycin (about 0.3%), Erythromycin, (about 5 mg/gm), and Tetracycline HCl (1%).

In a "triple antibiotic" form, the composition includes Polymyxin B, Neomycin Sulfate and Zinc Bacitracin. One or more agents are added to stabilize the Zinc Bacitracin, such as lidocaine HCl. The Lidocaine HCl can be present in about 1-4 wt. % of the amount of Zinc Bacitracin, such as about 400 to 500 units per gram. The base in these formulations holds the actives in an oil phase. Thus, a triple antibiotic form can include Polymyxin B Sulfate (about 5,000 to about 10,000 units/gm) Neomycin Sulfate (about 1.75 to about 3.5 mg/gm) and Zinc Bacitracin (about 400 to about 500 units/gm). These concentrations can be reduced by about 20% without loss of efficacy. A triple antibiotic form can include Polymyxin B Sulfate (about 4,000 to about 8,000 units/gm) Neomycin Sulfate (about 1.4 to about 2.8 mg/gm) and Zinc Bacitracin (about 320 to about 400 units/gm). In an exemplary embodiment, and effective amount of a triple antibiotic form is about 5 mg neomycin sulfate, about 5000 units polymyxin B sulfate and about 400 units bacitracin (per gram). Thus, an effective antibiotic includes, but is not limited to, 5 mg neomycin sulfate, 5000 units polymyxin B sulfate and 400 units bacitracin (per gram). Another effective antibiotic includes, but is not limited to, 4 mg neomycin sulfate, 4000 units polymyxin B sulfate and 320 units bacitracin (per gram).

Imidazoquinolines having Toll-Like Receptor 7 (TLR7) Ligand Activity

Imidazoquinolines are synthetic immunomodulatory drugs that act by binding toll-like receptors 7 and 8 (TLR7/TLR8) on dendritic cells, structurally mimicking these receptors' natural ligand, viral single-stranded RNA. An imidaxoquinoline is a double cyclic organic molecule; derivatives and salts thereof are included. The addition points for derivatives are illustrated below:

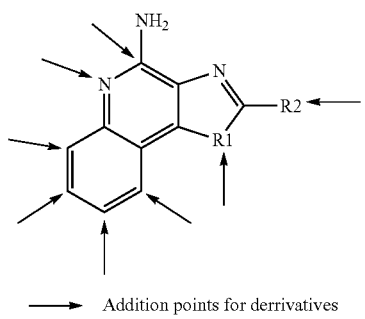

→ Addition points for derrivatives

Imiquimod and resiquimod are imidazoquinoline compounds (see Peet et al., J. Med. Chem., vol. 28, pp. 298-302, 1985). The compound characterized as 1-isobutyl-1H-imidazo[4,5-c]-quinolin-4-amine or 1-(2-methylpropyl)-1H-imidazo[4,5-c]quinolin-4-amine, and known as imiquimod, is disclosed in U.S. Pat. No. 4,689,338 and described therein as an antiviral agent and as an interferon inducer, which is incorporated herein by reference in its entirety. A variety of formulations for topical administration of imiquimod are also described therein. U.S. Pat. No. 4,689,338 is incorporated herein by reference in its entirety. U.S. Pat. No. 5,238,944; U.S. Pat. No. 7,038,051; U.S. Pat. No. 6,693,113; U.S. Pat. No. 6,894,060; U.S. Patent Publication No. 2007/0123558; and U.S. Patent Publication No. 2002/147210, disclose topical formulations and/or topical and transdermal delivery systems containing 1-isobutyl-1H-imidazo[4,5-c]-quinolin-4-amine or 1-(2-methylpropyl)-1H-imidazo[4,5-c]quinolin-4-amine, wherein each are incorporated herein by reference in their entireties.

The FDA has approved a 5% imiquimod cream, commercially available under the brand name ALDARA®, to treat certain dermal and mucosal associated conditions, such as (1) the topical treatment of clinically typical, nonhyperkeratotic actinic keratosis (AK) on the face or scalp in immunocompetent adults, (2) topical treatment of biopsy-confirmed, primary superficial basal cell carcinoma (sBCC) in immunocompetent adults, and (3) the topical treatment of external genital and perianal warts/condyloma acuminata in patients 12 years or older. Each gram of the ALDARA® 5% imiquimod cream contains 50 mg of imiquimod in an off-white oil-in-water vanishing cream base consisting of isostearic acid, cetyl alcohol, stearyl alcohol, white petrolatum, polysorbate 60, sorbitan monostearate, glycerin, xanthan gum, purified water, benzyl alcohol, methylparaben, and propylparaben. The cream is packaged in single-use packets or sachets, each containing 250 mg of cream, equivalent to 12.5 mg of imiquimod. Lower dose strengths of imquimod have also been untilized, for example, a pharmaceutical formulation containing imiquimod in an amount of between about 1.0 percent and about 4.25 percent by weight based on the total weight of the formulation, such as a pharmaceutical formulation containing imiquimod in an amount of about 2.5% or about 3.75% (see, for example, U.S. Published Patent Application No. 20110263634. These lower dose formulation include (a) imiquimod and (b) a fatty acid, e.g., isostearic, palmitic, stearic, linoleic, unrefined oleic acid or refined oleic acid, such as SUPER REFINED® oleic acid NF. Generally, these lower dose formulations include greater than 1 percent and to about 4.25 percent by weight of imiquimod, based on the total weight of the cream; about 5 percent to about 30 percent by weight of fatty acid, based on the total weight of the cream; and optional ingredients such as emollients, emulsifiers, thickeners, and/or preservatives. These doses are of use in the compositions disclosed herein. In some embodiments, the compositions disclosed herein include about 1 mg/gm to about 10 mg/gm imiquimod, such as about 2 mg/gm to about 7 mg/gm, such as about 5 mg/gm imiquimod.

A therapeutically effective amount of resiqumod (R-848, 1-[4-amino-2-(ethoxymethyl)imidazo[4,5-c]quinolin-1-yl]-2-methylpropan-2-ol) can also be included in the present compositions. Resiquimod is available as a 0.01% gel (3M Pharmaceuticals, St. Paul, Minn.). Methods for preparing resiquimod are known and disclosed in, for example, U.S. Pat. No. 5,389,640. Pharmaceutical formulations containing resiquimod and methods for preparing them are disclosed in U.S. Pat. No. 5,939,090. Other suitable formulations are known and can be used according to the invention including, for example, formulations disclosed in U.S. Pat. No. 6,245,776. The entire disclosure of each of these patents is incorporated herein by reference. Exemplary formulations include resiquimod in an amount about 0.001 to 0.05 percent by weight, such as about 0.01 percent by weight, based on the total weight of the formulation. These doses are of use in the compositions disclosed herein.

Additional hydroxyl, alkoxy, sulfonamide and sulfamide derivates that are imidazoquinolines are known, see for example, U.S. Pat. No. 6,518,265; and U.S. Pat. No. 4,689,338; all of which are incorporated herein by reference. For example, additional imidazoquinolones include:

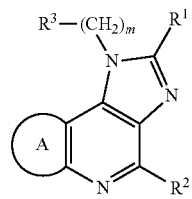

wherein $R^1$ represents hydrogen atom, hydroxyl group, an alkyl group which may have one or more substituents, a cycloalkyl group which may be substituted, a styryl group which may be substituted, or an aryl group which may have one or more substituents; $R^2$ represents hydrogen atom, an alkyl group, a halogen atom, hydroxyl group, an amino group which may have one or two substituents, a cyclic amino group which may be substituted, or a phenoxy group which may be substituted; ring A represents a benzene, cyclohexene, cyclopentene, or thiophene ring which may be substituted with one or more alkyl groups, alkoxy groups, or halogen atoms; $R^3$ represents a saturated nitrogen-containing heterocyclic group which may be substituted; and m represents an integer of from 0 to 3; provided that when $R^3$ represents unsubstituted piperidino group, at least one of $R^1$ and $R^2$ is not hydrogen atom. A therapeutically effective amount of any of these imidazoquinolones, or any other imidazoquinolones that have T2R7 ligand activity can be included in the compositions disclosed herein.

Surfactants

A wide variety of surfactants are useful in the presently disclosed compositions including, for example, ethoxylated non-ionic and ethoxylated ionic surfactants. Surfactants suitable for use include cetereths, ceteths, cetyl alcohol, deceths, dodoxynols, glyceryl palmitate, glyceryl stearate, laneths, myreths, nonoxynols, octoxynols, oleths, PEG-castor oil, poloxamers, poloxamines, polysorbates, ammonium laureth sulfate and sodium laureth sulfate. Other suitable surfactant/emulsifying agents would be known to one of skill in the art and are listed in the CTFA International Cosmetic Ingredient Dictionary and Handbook, Vol. 2, 7th Edition (1997). Sufactants include octoxynol-9 and include a polysorbate, such as Polypsorbate 20, Polysorbate 40, Polysorbate 60 or Polysorbate 80. Another surfactant is a pheoxypolyethoxyethanol (e.g., TRITON® X-100, X-301, X-165, X-102, and X-200, and TYLOXAPOL®) or sodium dodecyl sulfate.

The amount of surfactant present generally ranges from about 0% to about 10% v/v, such as from about 0.1% to about 10% v/v, for example, from about 1% to about 6% v/v. In several examples, the amount ranges from about 2% v/v to about 6% v/v, such as about 3% v/v to about 6% v/v, or from about 3% v/v to about 5% v/v. In several specific, non-liming examples the composition includes about 3% v/v to about 5% v/v of a polysorbate, such as Polysorbate 20, Polysorbate 40, Polysorbate 60 or Polysorbate 80.

In some embodiments, the composition comprises an emulsifying agent to aid in the formation of emulsions. Emulsifying agents include compounds that aggregate at the oil/water interface to form a kind of continuous membrane that prevents direct contact between two adjacent droplets. Certain embodiments feature oil-in-water emulsion compositions that may readily be diluted with water to a desired concentration without impairing their anti-pathogenic properties. In addition to discrete oil droplets dispersed in an aqueous phase, oil-in-water emulsions can also contain other lipid structures, such as small lipid vesicles (e.g., lipid spheres that often consist of several substantially concentric lipid bilayers separated from each other by layers of aqueous phase), micelles (e.g., amphiphilic molecules in small clusters of 50-200 molecules arranged so that the polar head groups face outward toward the aqueous phase and the apolar tails are sequestered inward away from the aqueous phase), or lamellar phases (lipid dispersions in which each particle consists of parallel amphiphilic bilayers separated by thin films of water). These lipid structures are formed as a result of hydrophobic forces that drive apolar residues (e.g., long hydrocarbon chains) away from water.

The above lipid preparations can generally be described as surfactant lipid preparations (SLPs). SLPs are minimally toxic to mucous membranes and are believed to be metabolized within the small intestine (See e.g., Hamouda et al., J. Infect. Disease 180:1939, 1998). SLPs are non-corrosive to plastics and metals in contrast to disinfectants such as bleach. As such, formulations based on SLPs are contemplated to be particularly useful against bacteria, fungi, viruses and other pathogenic entities, see U.S. Pat. No. 6,559,189.

Other Agents

For certain embodiments, the topical formulations of the invention can include an antioxidant. Suitable antioxidants are those that are pharmaceutically acceptable and described in the International Cosmetic Ingredient Dictionary and Handbook, Ninth Edition, Volume 4, 2002, and in the USP NF 2004: The United States Pharmacopeia, 27.sup.th Revision and The National Formulary, $22^{nd}$ Edition. Examples of suitable antioxidants include ascorbic acid (D and/or L enantiomers), ascorbyl palmitate (D and/or L enantiomers), butylated hydroxyanisole (BHA), butylated hydroxytoluene (BHT), cysteine (D and/or L enantiomers), propyl gallate, sodium formaldehyde sulfoxylate, sodium thiosulfate, and tocopherol. For certain embodiments, the antioxidant is selected from the group comprising aromatic hydroxy groups capable of hydrogen atom donation. Examples of such antioxidants include BHA, BHT, propyl gallate, and tocopherol. In additional embodiments, the antioxidant is selected from the group consisting of BHA, BHT, and combinations thereof. For certain embodiments, the antioxidant is BHA.

The formulation also can include a preservative system. The preservative system includes one or more compounds that inhibit microbial growth (e.g., fungal and bacterial growth) within the formulation (for example, during manufacturing and use). The preservative system will generally include at least one preservative compound, such as, for example, methylparaben, ethylparaben, propylparaben, butylparaben, benzyl alcohol, phenoxyethanol, and sorbic acid or derivatives of sorbic acid such as esters and salts. Various combinations of these compounds can be included in the preservative system. In some embodiments of the invention, the preservative system includes methylparaben, propylparaben and benzyl alcohol.

In some embodiments of the invention, the preservative compound is present in an amount of at least 0.01% by weight, such as for example, at least 0.02%, at least 0.03%, at least 0.04%, and at least 0.05%, by weight based on the total weight of the formulation. In other embodiments of the invention the preservative compound is present in an amount of at most 3%, such as for example, at most 2.5%, at most 2.0%, at most 1.0%, at most 0.5%, at most 0.4%, at most 0.3%, and at most 0.2%, by weight based on the total weight of the formulation.

Optionally, the formulation can contain additional pharmaceutically acceptable excipients such as humectants, such as for example, glycerin; chelating agents, such as for example, ethylenediaminetetraacetic acid; and pH adjusting agents, such as for example, potassium hydroxide or sodium hydroxide.

The formulations can also comprise a viscosity-enhancing agent. Examples of suitable viscosity enhancing agents include long chain alcohols, for example, cetyl alcohol, stearyl alcohol, cetearyl alcohol; cellulose ethers such as hydroxypropylmethylcellulose, hydroxyethylcellulose, hydroxypropylcellulose, and carboxymethylcellulose; polysaccharide gums such as xanthan gum; and homopolymers and copolymers of acrylic acid crosslinked with allyl sucrose or allyl pentaerythriol such as those polymers designated as carbomers in the United States Pharmacopoeia. Suitable carbomers include, for example, those available as CARBOPOL 934P, CARBOPOL 971P, CARBOPOL 940, CARBOPOL 974P, CARBOPOL 980, and PEMULEN TR-1 (USP/NF Monograph; Carbomer 1342), all available from Noveon, Cleveland, Ohio.

The amount of the viscosity enhancing agent, when used, is at least 0.1% by weight, at least 0.2% by weight, at least 0.5% by weight, at least 0.6% by weight, at least 0.7% by weight, at least 0.9% by weight, or at least 1.0% by weight, based on the total weight of the formulation. In certain embodiments, the amount of the viscosity-enhancing agent, when used, is at most 10% by weight, at most 5.0% by weight, at most 3.0% by weight, at most 2.0% by weight, or at most 1.5% by weight, based on the total weight of the formulation.

Thus, in some embodiments, these compositions that are formulated for topical administration include additional compounds. In some embodiments, these additional agent are admixed into either the aqueous or oil phases of the composition. In other embodiments, these additional compounds are admixed into a composition of previously emulsified oil and aqueous phases. In certain of these embodiments, one or more additional compounds are admixed into an existing emulsion composition immediately prior to its use. In other embodiments, one or more additional compounds are admixed into an existing emulsion composition prior to the compositions immediate use.

Although topical formulations, such as creams and salves formulated for dermal and ocular delivery are contemplated, the delivery systems can include time-release, delayed release or sustained release delivery systems. Such systems can avoid repeated administrations of the compositions, increasing convenience to the subject and the physician. Many types of release delivery systems are available and known to those of ordinary skill in the art. Specific examples include, but are not limited to: (a) erosional systems such as those described in U.S. Pat. Nos. 4,452,775; 4,667,014; 4,748,034; 5,239,660; and 6,218,371 and (b) diffusional systems in which an active component permeates at a controlled rate from a polymer such as described in U.S. Pat. Nos. 3,832,253 and 3,854,480.

The delivery system can include collagen, fibrin, or a membrane extract, such as a basal membrane extract, for example wherein the composition is formulated for administration to the skin. Suitable basement membrane extracts include a biologically active polymerizable extract containing in parts by weight about 60-85% laminin, 5-30% collagen IV, 1-10% nidogen, 1-10% heparan sulfate proteoglycan and 1-5% entactin (see U.S. Pat. No. 4,829,000, incorporated herein by reference, which discloses BME compositions as well as methods for producing these compositions). BME can support normal growth and differentiation of various cell types including epithelial cells when cultured. Basal membrane extracts are well known in the art and are commercially available.

For ophthalmic administration, such as for administration to the cornea, the carrier must be suitable for application to the eyes. Preparation of suitable ophthalmic solutions requires careful consideration of factors such as isotonicity, the need for buffering agents, the need for preservatives, and sterilization. Lacrimal fluid is isotonic with blood, having an isotonicity value corresponding to that of a 0.9% sodium chloride solution. Ideally, an ophthalmic solution should have this isotonicity value, but eyes can tolerate isotonicity values as low as that of a 0.6% sodium chloride solution and as high as that of a 2.0% sodium chloride solution without substantial discomfort. Some ophthalmic solutions are necessarily hypertonic in order to enhance absorption and provide a concentration of the active ingredients to exert a prompt and effective action. Suitable ophthalmic carriers include ointments, saline solutions, isotonic saline solutions, such as SORBI-CARE™ (Allergan Pharmaceuticals), NEO-DECADRONE™. (Merck, Sharp, and Dhome) and the like. Suitable ointments bases include LACRILUBE™.

Other suitable ophthalmic vehicles include boric acid which has a pH slightly below 5.0. Phosphate buffer system may also be employed and adjusted for isotonicity may provide a choice of pH ranging from about 5.9 to 8.0. Pharmaceutical grade of methyl cellulose may also be employed having a variable viscosity.

Methods are also provided for producing the disclosed compositions. The methods include heating a petroleum based composition comprising the antibiotic to a temperature of about 55° C. to about 70° C., such as about 60° C. to about 65° C., such as to about 65° C. Once the petroleum based composition is heated, an aqueous solution comprising the immunostimulatory K-type CpG ODN, the imidazoquinoline and a surfactant, such as, but not limited to polysorbate 20, polysorbate 40, polysorbate 60 or polysorbate 80 is added to achieve the desired concentration. The petroleum based composition is mixed with the aqueous solution to form an emulsion. The mixing can be achieved by any method, including sonication, vortexing, or shaking. Once the emulsion is produced it is cooled to room temperature. The composition can then be stored at room temperature, or at about 4° C.

Methods of Use

Methods of treating a wound are disclosed herein. The wound can be a wound in the skin, or a wound on any surface, including, but not limited to, the eye. Thus, the present methods utilize topical dermal or ocular administration. Generally, the composition is formulated for topical administration. The methods include administering to a subject of interest, such as a subject with a wound, an effective amount of a composition as disclosed herein. These compositions include an effective amount of 1) an imidazoquinoline having toll-like receptor 7 (TLR7) ligand activity, 2) an immunostimulatory K-type CpG oligodeoxynucleotide (ODN) comprising an unmethylated CpG motif, 3) an antibiotic, and 4) a surfactant. The application of the composition results in accelerated wound healing, and also controls bacterial infections at the site of the wound.

For treatment of the skin or eye, a therapeutically effective amount of the composition can be locally administered to the affected area. The pharmacological compositions disclosed herein facilitate the use of at least one K ODN, an antibiotic and an imidazoquinoline, either in vivo or ex vivo, to promote wound healing. Such a composition can be suitable for delivery of the active ingredient to any suitable subject, and can be manufactured in a manner that is itself known, e.g., by means of conventional mixing, dissolving, granulating, emulsifying, encapsulating, entrapping or lyophilizing processes. Pharmacological compositions can be formulated in a conventional manner using one or more pharmacologically (e.g., physiologically or pharmaceutically) acceptable carriers, as well as optional auxiliaries that facilitate processing of the active compounds into preparations which can be used pharmaceutically, as discussed above.

Topical compositions to heal wounds, such as dermal wounds, are disclosed herein. These wounds amenable to treatment may be of superficial nature or may be deep and involve damage of the dermis and the epidermis of skin. Thus, methods are provided to promote wound healing in a subject. The composition can be applied directly to the target location, for example in a topical preparation such as an ointment, or as a part of a dressing or a bandage.

Thus, compositions disclosed herein are be useful for treating cutaneous wounds affecting the epidermal and dermal layers of the skin, as well as injuries to the cornea and epithelial-lined hollow organs. The method disclosed herein are of use to treat corneal and scleral wounds, including wounds which affect the epithelial layer, stromal layer and endothelial layers of the eye. The method can include selecting these subjects.

For use in wound treatment, the compositions will usually have a concentration in the range described above. The compositions are usually be applied to the affected area periodically, typically from about 1 to 12 times each day, such as, for example, over a period of from about 3 to 14 days, depending on the nature of the wound. In some cases, it may be desirable to apply the compositions indefinitely. The composition affects both bacterial load and the rate of wound healing. In some embodiments, the composition increases wound healing at least 20%, at least 30%, at least 40%, at least 50%, at least 60%, at least 70%, at least 80%, at least 90%, at least 95%, at least 100% or at least 200%, as compared to a control, such as a standard value, the rate of wound healing in the presence of antibiotic alone, or the rate of wound healing achieved with the antibiotic and imiquimod, but in the absence of a CpG ODN.

The compositions can also be used in the treatment of a surgical wound and other intentional interventions where the compositions may be applied immediately after completion of the surgery.

The subject can be any mammalian subject of interest, including a human or a veterinary subject. The subject can be a child or an adult subject, such as a young, middle aged, or older adult subject. In humans, an adult subject is greater than 18 years of age, a young adult is about 18 to about 35 years of age, a middle aged adult is generally considered to be about 35 to about 55 years of age, and an elderly (or aged) human subject is more than about 55 years old, such as more than 60 years old, more than 65 years old, more than 70 years old, more than 75 years old or more than 80 years old.

The subject can heal wounds at a normal rate or can be healing impaired. Generally, the present compositions provide increased healing as compared to treatment with antibiotic alone. In one embodiment, the presently disclosed compositions provided accelerated wound healing as compared to the treatment of the same subject using an antibiotic alone. In other embodiments, the presently disclosed compositions also provide accelerated healing as compared to administration of an antibiotic and an imidazoquinoline (for example, imiquimod or resiquimod), but in the absence of the immunostimulatory K-type CpG ODN. In other embodiments, the presently disclosed compositions also provide accelerated healing as compared to administration of an antibiotic and the immunostimulatory K-type CpG ODN, but in the absence of imidazoquinoline (for example, imiquimod or resiquimod).

A number of afflictions and conditions can result in healing impairment. These include diabetes (such as Type II diabetes mellitus), treatment with both steroids and other pharmacological agents, and ischemic blockage or injury (as in peripheral vascular disease or traumatic vascular occlusion). Conditions which induce abnormal wound healing, include, but are not limited to uremia, malnutrition, vitamin deficiencies, obesity, infection, immunosuppression and complications associated with systemic treatment with steroids, radiation therapy, and antineoplastic drugs and antimetabolites. Steroids which have been shown to impair wound healing include cortisone, hydrocortisone, dexamethasone, and methylprednisolone. Non-steroid compounds, such as octreotide acetate, have also been shown to impair wound healing (Waddell et al., Am. Surg. 63:446 449, 1997). Thus, the methods disclosed herein are of use to promote wound healing in a subject has impaired wound healing, such as due to disease. The methods can include selecting the subject with impaired wound healing, such as a subject with one of the conditions listed above.

Methods are provided for stimulating healing of wounds including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, and burns resulting from heat exposure or chemicals. Methods are also provided for wounds that result from ischemia and ischemic injury, such as chronic venous leg ulcers caused by an impairment of venous circulatory system return and/or insufficiency. The compositions disclosed herein can be used to promote dermal reestablishment subsequent to dermal loss while controlling infection. In addition, a therapeutically effective amount of the compositions can be used to increase the tensile strength of epidermis and epidermal thickness. Thus, the disclosed methods are of use in stimulating the healing of different types of wounds in normal subjects and subjects that have impaired wound healing while controlling or eliminating bacterial growth. The method can include selecting any one of the subjects of interest, such as those with any wound.

Methods are also provided herein to increase the adherence of skin grafts to a wound bed and to stimulate re-epithelialization from the wound bed. Types of grafts include, but are not limited to: autologous skin graft, artificial skin, allografts, autodermic graft, autoepidermic grafts, avascular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. The methods include administering to the subject with the graft a therapeutically effective amount of the compositions disclosed herein, thereby increasing the adherence and acceptance of the graft and controlling or eliminating bacterial growth. In some embodiments, cells or a tissue treated with the composition are transplanted into a subject. In one specific, non-limiting example, the composition is administered to a graft, such as a skin graft, prior to transplantation.

Methods are also provided to treat blisters and burns due to abrasion or chemical injury. These methods include the treatment of the skin or internal organs. These methods include treatment of ovary injury, for example, due to treatment with chemotherapeutics or treatment with cyclophosphamide; radiation- or chemotherapy-induced cystitis; or high-dose chemotherapy-induced intestinal injury. The methods include administering to the subject a therapeutically effective amount of a composition as disclosed herein to promote healing of the blisters or burns and to reduce or eliminate bacterial growth.

Methods are provided for promoting the healing of anastomotic and other wounds caused by surgical procedures in individuals. These methods include administration of an effective amount of the compositions disclosed herein, after, and/or during anastomotic or other surgery. Anastomosis is the connecting of two tubular structures, for example, when a mid-section of intestine is removed and the remaining portions are linked together to reconstitute the intestinal tract. Unlike cutaneous healing, the healing process of anastomotic wounds is generally obscured from view. Further, wound healing, at least in the gastrointestinal tract, occurs rapidly in the absence of complications; however, complications often require correction by additional surgery (Thornton and Barbul, Surg. Clin. North Am. 77:549 573

(1997)). The method can include selecting a subject in need of anastomotic wound healing. The subject can be a subject with impaired wound healing due to one of the conditions above, or can be a subject that has normal wound healing, such as a subject that does not have any of the conditions listed above.

The disclosure is illustrated by the following non-limiting Examples.

EXAMPLES

Pathogenic bacteria are recognized by cells expressing Toll-like receptors (TLRs). This interaction initiates an innate immune response that increases host resistance to infection and accelerates wound healing. Antibiotics that eliminate bacteria have a detrimental effect on the rate of wound repair. The antibiotic treatment i) eliminates bacteria from the skin, ii) reduces wound inflammation (as manifest by decreased expression of IL-1β, CCL2, IFNa and IFNb mRNA) and thereby iii) delays wound healing. The work below documents that this adverse consequence of antibiotics is corrected by co-administering a TLR9 ligand, such as CpG ODN and/or a TLR7 ligand, such as imiquimod.

Example 1

Materials and Methods

Mice:
Specific pathogen free female BALB/c mice were studied at 8-12 weeks of age. Animals were monitored daily by veterinarians.

Reagents:
Phosphorothioate K-type CpG ODN 1555 (sequence: GCTAGACGTTAGCGT, SEQ ID NO: 30) was synthesized and was free of endotoxin and protein contamination. Imiquimod was purchased from INVIVOGEN® (San Diego, Calif.) triple antibiotic ointment containing 5 mg neomycin sulfate, 5000 units polymyxin B sulfate and 400 units bacitracin emulsified in one gram of white petrolatum was obtained from FOUGERA® (Melville, N.Y.). In some studies, 5 µl of CpG ODN (10 mg/ml) and/or 5 µl (1 mg/ml) was added to 100 µl of antibiotic ointment. This formulation was then heated to 65° C. and vigorously mixed to emulsify.

Murine In Vivo Wound Repair Model:
The wound repair model of Devalaraja et al (J Invest Dermatol 2000; 115: 234-44) was used. Skin on the back was shaved and treated antibiotic ointment or petrolatum. In some studies, mice were injected s.c. at the base of the tail with 50 ug/g of vancomycin and imipenrm/cilastatin (Fernandez et al., Antimicrob Agents Chemother 2010; 54: 116-25, 2010). Fourteen days later, the mice were anesthetized by intraperitoneal injection of ketamine (80 µg/g) plus xylazine (10 ug/g). The skin on the back was gently cleaned with PBS. A 6 mm full-thickness excisional punch biopsy (including the *Pannilulus carnosus*) was taken using an ACU-PUNCH® (Fort Lauderdale, Fla.) from the right and left upper paravertebral region of each animal. Individual biopsy sites were coated with 100 µl of antibiotic ointment±50 µg CpG ODN and/or 5 µg IMQ, and then covered with nonadhesive sterile gauze (Sato et al., Wound Repair Regen 2010; 18: 586-93). Mice were wrapped with a form-fitting bandage to further protect the biopsy sites. Wound contraction was recorded every other day by digital photography and changes calculated using NIH Image J software (available on the internet, version 1.37). Each treatment was tested and results averaged in a minimum of five independent animals/group.

Quantitative RT-PCR:
Tissue from the biopsy site was excised, homogenized in Trizol, and extracted with chloroform. Total RNA was isolated from the aqueous phase and passed through an RNEASY® column as per manufacturer's suggestion (QIAGEN®, Valencia, Calif.). 1 µg of total RNA was reverse-transcribed using the QUANTITECT™ Reverse Transcription. Kit (QIAGEN®). Purified cDNA was used as the template for quantitative RT-PCR conducted using pre-designed primer/probe sets for interleukin (IL)-1β, CCL2, IFNa, IFNβ, basic fibroblast growth factor (FGF), transforming growth factor (TGF)β, and glyceraldehyde 3-phosphate dehydrogenase (GAPDH) (Applied Biosystems, Foster City, Calif.). Gene expression levels were analyzed using the STEPONEPLUS™ RT-PCR system (APPLIED BIOSYSTEMS®). All reagents and probes used in this system were purchased from APPLIED BIOSYSTEMS®.

Bacterial Genomic DNA Extraction:
Mice were anesthetized by intraperitoneal (i.p.) injection of ketamine (80 mg/kg) plus xylazine (10 mg/kg). Samples from the wound area were collected using CATCH-ALL™ Sample Collection Swabs (EPICENTRE® Biotechnologies, Madison, Wis.). The swab was moistened with enzymatic lysis buffer, rubbed over the sample area, and then incubated with 180 µl of enzymatic lysis buffer and 0.5 ul READY-LYSE™ Lysozyme Solution (EPICENTRE® Biotechnologies) for 1 hr at 37° C. Genomic DNA was extracted from each swab using the DNEASY® kit (QIAGEN®).

Quantitative Real-Time PCR Amplification of 168 rRNA Gene:
The amount of 16S rRNA gene was measured. In brief, QT-PCR was performed using a QUANTITECT™ SYBR® Green PCR Kit (QIAGEN®). The PCR amplifications started at 95o for 3 min, followed by 40 cycles of 10 s at 95° C. and 45 s at 63° C. using the 16S rRNA gene universal primers (UniF340 ACTCCTACGGGAGGCAGCAGT (SEQ ID NO: 36), UniR514 ATTACCGCGGCTGCTGGC (SEQ ID NO: 37)). Absolute quantitation of bacterial DNA was achieved by comparison to a standard curve generated by subjecting serial dilutions of a known amount of *E coli* DH5a genomic DNA to precisely the same QT-PCR regimen.

Statistical Analysis:
Statistical analysis was performed using SIGMASTAT®, version 3.11 (SYSTAT® Software, Inc., Chicago, Ill.). Differences in the rate of healing of Bx sites were assessed using one way repeated measures analysis of variance (ANOVA). The area under the curve was calculated for overall changes in wound area using serial measurement. P values<0.05 were considered significant for all analyses. All values are expressed as means±SE unless otherwise noted.

Example 2

Effect of Antibiotic Treatment on Wound Healing

The effect of various concentrations of polysorbate (ranging from 1-10%) on the ability of the ODN and IMQ dissolved in water to form a stable emulsion with the liquified antibiotic ointment was tested. A ratio of 5% polysorbate:85% liquified ointment:10% TLR ligand yielded an emulsion from which the active components were slowly released (over a period of 2 days) and in a form that retained their biological activity (as well as the antibacterial activity of the ointment).

Triple antibiotic ointment containing neomycin, bacitracin and polymyxin B was applied to either the right or left dorsum of mice while antibiotic-free petrolatum (the base in which the ointment was formulated) was administered to the contralateral side. Alternatively, the broad spectrum antibiotics vancomycin and imipenem/cilastatin were injected at the base of the tail to examine the effect of systemic therapy. Bacterial levels were monitored by swabbing the skin and quantifying 16 s bacterial rRNA by QT-PCR (Singer and Dagurn, N Engl J Med 2008; 359: 1037-46). As shown in FIG. 1, both local and systemic antibiotic therapy reduced bacterial contamination (reflected by decreased levels of 16s rRNA) by >99% and >96%, respectively ($p<0.05$).

A well-established murine model of wound healing was used to evaluate the effect of antibiotic treatment on the rate of wound repair (Devalaraja et al., J Invest Dermatol 2000; 115: 234-44). Identical full-thickness excisional biopsies were taken from skin sites treated with either antibiotic ointment or petrolatum (different treatments were administered to contralateral sides of each animal). Sequential photographs provided a permanent record of the speed of wound closure. Untreated biopsy sites and sites treated with petrolatum (ointment control), healed at nearly identical rates. In contrast, sites treated with antibiotic ointment healed significantly more slowly, lagging behind control sites by approximately 2 days ($p<0.001$, FIG. 2A). Thus, topical antibiotic treatment significantly reduced both bacterial load and the rate of wound healing. A similar result was observed in mice treated by systemic injection of antibiotics, with average wound healing being delayed by 1.8 days ($p<0.001$, FIG. 2B).

Example 3

Effect of TLR7 and TLR9 Ligands on Wound Healing

TLR ligands can accelerate wound healing in normal mice and non-human primates (see, for example, Sato et al., Wound Repair Regen 2010; 18: 586-93). It was postulated that the slowing of wound healing associated with antibiotic therapy might be reversed by co-delivering the TLR9 ligand CpG ODN and/or the TLR7 ligand imiquimod.

Figure 5:
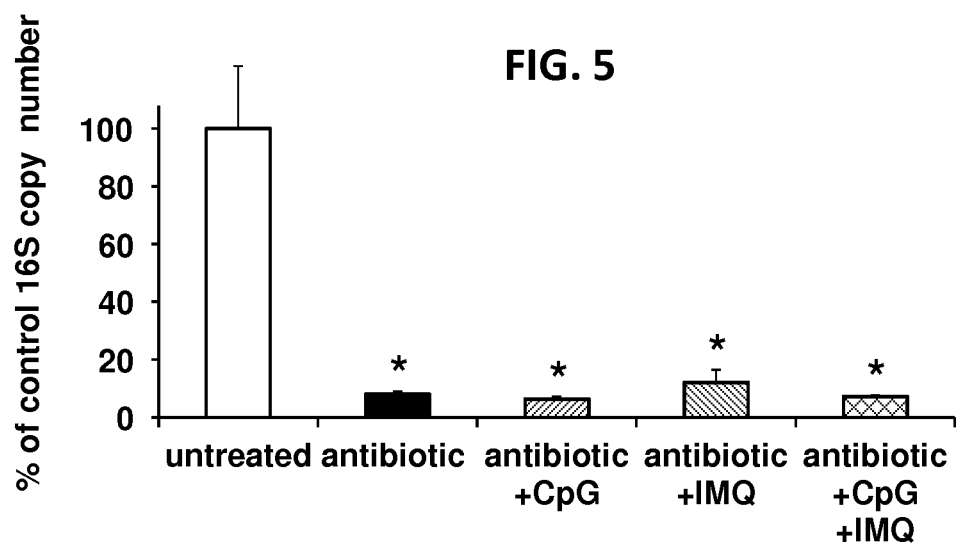
FIG. 5 is a bar graph illustrating a quantitative analysis of bacterial DNA on skin. Mice were treated with antibiotic ointment+50 μg or 5 μg of IMQ as described in FIG. 3. Bacterial DNA was isolated and analyzed as described in FIG. 1. Results represent the mean±SE of at least 4 independent samples/treatment group. *p<0.05 vs untreated group.

Preliminary studies were performed to identify the optimal method of co-administering these ligands with the antibiotic ointment. Simply applying CpG ODN or IMQ over a pre-existing layer of antibiotic ointment or petrolatum had no effect on wound healing, suggesting that their diffusion to the skin was blocked. A method for incorporating the CpG ODN and/or IMQ into the antibiotic ointment was then developed, in which the ointment was melted and vortexed together with the TLR ligand. Once cooled to room temperature (RT), the bioactivity of the antibiotic and TLR ligand were retained (FIG. 5) with the ligand diffusing out of the ointment over a period of 2-3 days.

The wound healing protocol described above was repeated using the TLR-formulated ointments. Results from independent experiments showed that incorporating CpG ODN and/or IMQ into the ointment completely corrected the delay in wound healing caused by the antibiotic alone ($p<0.001$ for both TLR ligands, FIG. 3). The effect was greatest at the early time points (FIG. 3). Indeed, 25% wound closure was achieved after 3.7±0.5 days at sites treated with antibiotic ointment+CpG ODN, 3.2±0.2 days at sites treated with antibiotic ointment+IMQ versus 5.4±0.6 days at sites treated with antibiotic ointment alone (FIG. 3). Co-incorporating both CpG ODN plus IMQ with the antibiotic led to 25% wound closure after 2.4±0.3 days.

Example 4

Effect of Antibiotic Plus TLR Ligands on IL-1β, CCL2, IFNa and IFNβ Production

Figure 4:
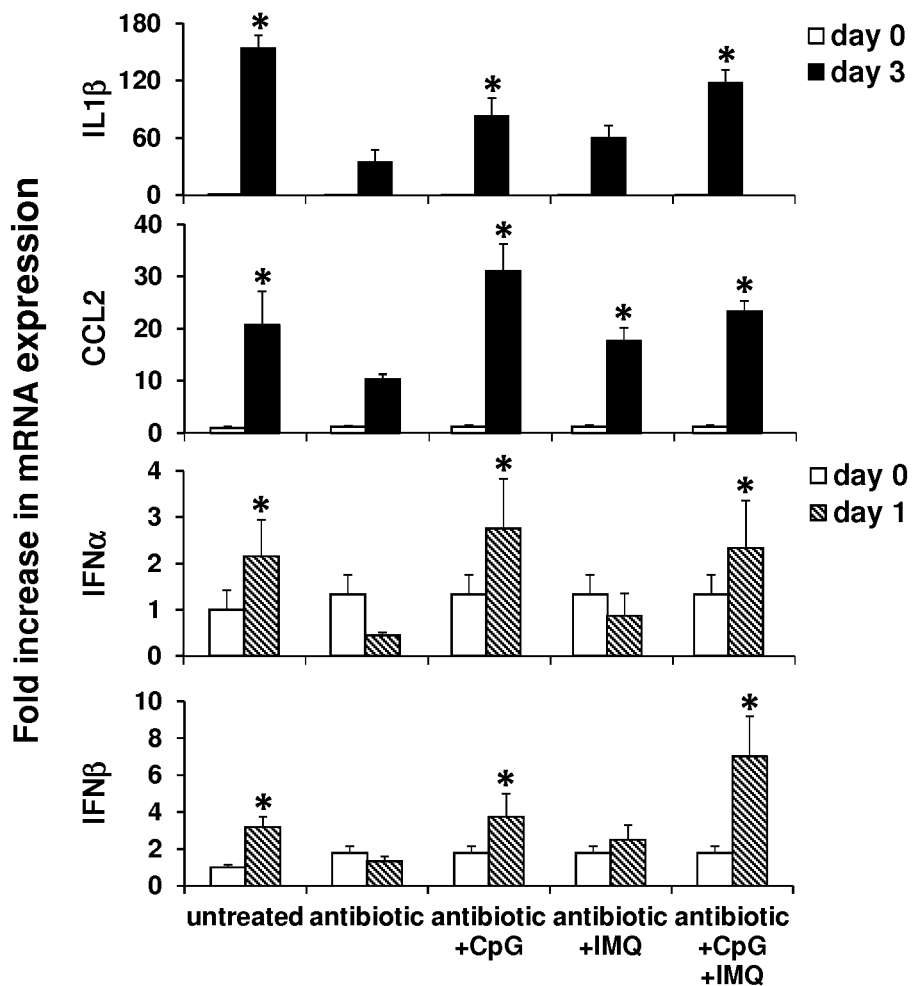
FIG. 4 is a set of bar graphs showing the effect of antibiotic plus TLR ligands on cytokine/chemokine mRNA levels at the wound site. Excisional biopsies were taken from the right and left dorsum of mice treated with antibiotic ointment co-formulated with CpG ODN and/or IMQ. Total RNA was extracted at the time of biopsy (Bx) or 3 days later. IL-1β, CCL2, IFNa and IFNβ mRNA levels were determined by quantitative RT-PCR, as corrected for the GAPDH house keeping gene. Data show the change in mRNA concentration relative to the untreated control group on day 0. Results represent the mean±SE of at least 4 independent samples/treatment group. *p<0.05 vs antibiotic treated sites.

Previous studies showed that the expression of IL-1β, CCL2, IFNa and IFNβ at wound sites correlated with the rate of healing (Low et al., Am J Pathol 2001; 159: 457-63; Gregoria et al., J Exp Med 2010; 207: 2921-30; Shephard et al., Am J Pathol 2004; 164: 2055-6). mRNA was therefore isolated from biopsy sites and analyzed for levels of each factor. Consistent with previous findings, the concentration of IL-1β and CCL2 were significantly elevated 3 days post excisional Bx (FIG. 4). By comparison, wound sites treated with antibiotic alone had levels of IL-1β and CCL2 mRNA reduced by 4.5-fold and 2.1-fold, respectively ($p<0.05$). The addition of CpG ODN and to a lesser extent IMQ corrected these defects ($p<0.05$, FIG. 4). Similarly, antibiotic treatment reduced the expression of IFNa and IFNβ at the biopsy site, an effect reversed by the administration of either TLR ligand (FIG. 4).

Topical antibiotics are widely used to prevent wound infection. Current results show that the use of local or systemic antibiotics reduces bacterial burden in the skin but also slows the healing process. The latter undesirable outcome was prevented by adding TLR9 and/or TLR7 ligands to the antibiotic, yielding a combination product that both prevented infection and accelerated wound repair.

The local or systemic administration of broad spectrum antibiotics reduced the number of commensal skin bacteria by >99% and >95%, respectively (FIG. 1). Several observations link this effect to a subsequent slowing in wound healing (FIG. 2A). First, the petrolatum base used to formulate the ointment had no significant effect on either bacterial load or wound repair. Second, the effects were observed after either local or systemic antibiotic administration (FIG. 1 and FIG. 2B). Third, antibiotic treatment had no effect on the expression of TLR receptors in the skin (FIG. 7).

Synthetic ODN expressing unmethylated CpG motifs (patterned after the immunostimulatory sequences present in bacterial DNA) trigger the innate immune system via TLR9 (Drug News Perspect 2000; 13: 289-9; Krieg et al., Nature 1995; 374: 546-8). CpG ODN rapidly up-regulate the expression of pro-inflammatory genes (including IL-1β, CCL2, etc. (Klinman et al., J Leukoc Biol 2008; 84: 958-64; Kneufemann et al., Respir Res 2007; 8: 72; Mitchell et al., Mol Immunol 2010; 47: 2065-73. Furthermore, topical administration of CpG ODN significantly accelerated wound closure in mice and macaques (Sato et al., Wound Repair Regen 2010; 18: 586-93; Yamamoto et al., Biomaterials 2011; 32: 4238-42). This effect required the expression of TLR9 and its downstream signaling pathways (see, for example, Sato et al., supra). IMQ, a TLR7 ligand, also activates the innate immune system and promotes the production pro-inflammatory cytokines (including IL-1B) and chemokines (including CCL2) (Mitchell and Olive, Mol Immunol 2010; 47: 2065-73), although the effect of IMQ on wound healing was not previously examined.

Results show that the delay in wound healing caused by antibiotics was reversed by the co-administration of CpG ODN and/or IMQ (FIG. 3). The combination of CpG ODN plus IMQ accelerated wound repair more rapidly that either ligand alone.

Multiple factors contribute to the process of wound healing. IL-1β, CCL2 and IFNa/β are rapidly produced at wound sites, accelerate wound repair, and down-regulated by antibiotic therapy (FIG. 4). However, in addition to IL-1β, CCL2 and IFNa/β, additional cytokines, chemokines and growth factors contribute to the wound healing process.

Figure 6:
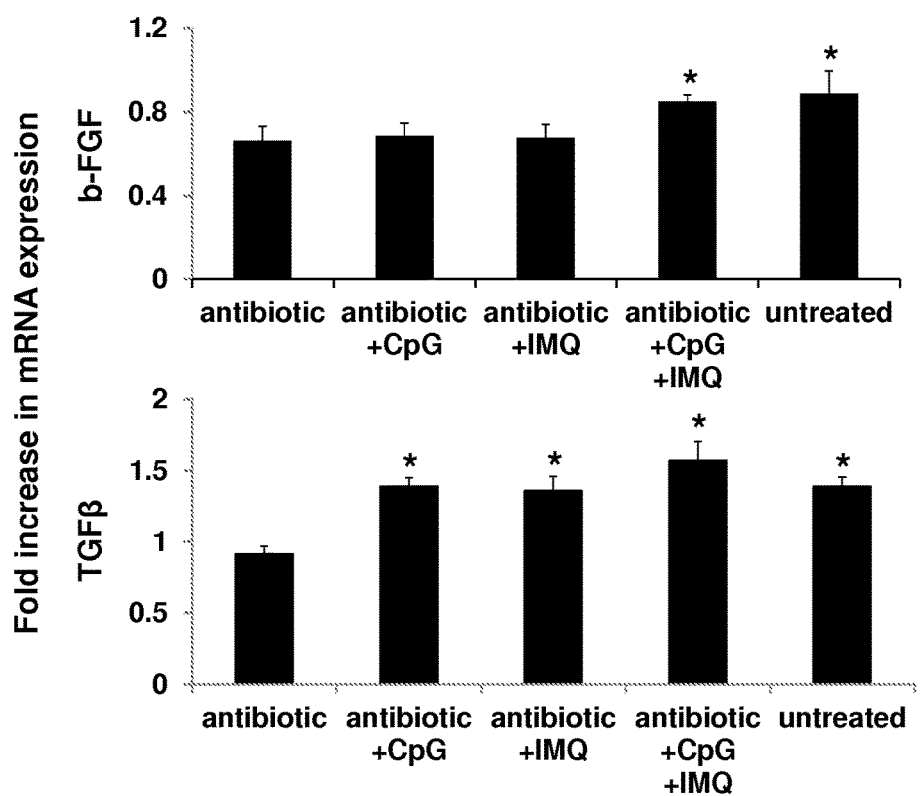
FIG. 6 is a bar graph of the effect of antibiotic ointment on the levels of b-FGF and TGFβ mRNA. Mice were treated as described in FIG. 3. Total RNA was extracted from the Bx sites on day 3. Quantitative RT-PCR was performed to detect b-FGF and TGFβ. Results represent the mean±SE of at least 4 independent samples/treatment group. *p<0.05 vs untreated group.

CpG ODN stimulate the production of b-FGF and VEGF (see, for example, Yamamoto et al., 2011, supra). Although antibiotic treatment did not reduce on the production of those factors, their expression at the wound site was increased by CpG ODN and IMQ administration (FIG. 6). These TLR ligands also up-regulated the expression of mRNA encoding TGFβ (FIG. 6), TGFβ levels typically increase during the early phase of wound healing, as this factor contributes to the recruitment of inflammatory cells, angiogenesis, collagen production, and wound remodeling (Mauyiel et al., J Biol Chem 1996; 271: 10917-23; Papakonstantinou et al, Cytokine 2003; 24: 25-35; Riedel et al., Arch Med Res 2007; 38: 45-51).

This work presented herein documents a side effect of antibiotic therapy: by eliminating skin bacteria, antibiotics reduce PAMP-dependent activation of the innate immune system, thereby reducing the rate of wound healing. This undesirable side effect was prevented by the co-administration of CpG ODN and/or IMQ. Without being bound by theory, these TLR ligands can replace the missing PAMPs and stimulate the production of inflammatory cytokines and chemokines that accelerate wound closure.

As cleansing or sterilizing skin wounds is a universally accepted clinical practice, there have been no studies examining the effect of skin bacteria on wound healing in humans. Several groups have examined whether topical antibiotics influence wound infection rates, and found no significant effect. As the wounds evaluated in those studies were pre-treated with alcohol and/or chlorhexidine to eliminate bacteria, they do not provide insight on the effect of PAMPs on wound closure (Smack et al., J Am Med Assoc 1996; 276: 972-7; Trookman et al., J Am Acad Dermatol 2011; 64: S8-15; Taylor et al., J Am Acad Dermatol 2011; 64: S30-35). It is only the present work that documents this effect of antibiotics, and provides strategies to counteract these effects.

It will be apparent that the precise details of the methods or compositions described may be varied or modified without departing from the spirit of the described invention. We claim all such modifications and variations that fall within the scope and spirit of the claims below.

We claim:

1. A pharmaceutical composition comprising an effective amount of 1) an imidazoquinoline having toll-like receptor 7 (TLR7) ligand activity, 2) an immunostimulatory K-type CpG oligodeoxynucleotide (ODN) comprising an unmethylated CpG motif, 3) an antibiotic, and 4) a surfactant, wherein the composition is formulated for topical administration, wherein the amount of the K-type ODN and the imidazoquinoline is sufficient to counteract wound healing delay caused by the antibiotic, and wherein the immunostimulatory K-type CpG ODN comprises an immunostimulatory CpG motif that has the formula:

$$5'N_1N_2N_3D\text{-}CpG\text{-}WN_4N_5N_6\ 3' \quad \text{(SEQ ID NO: 2)}$$

wherein (a) the central CpG motif is unmethylated,
(b) D is T, G or A, W is A or T,
(c) $N_1$, $N_2$, $N_3$, $N_4$, $N_5$, and $N_6$ are any nucleotides.

2. The composition of claim 1, wherein the immunostimulatory K-type CpG ODN comprises multiple CpG motifs, and wherein at least one nucleotide separates consecutive CpG motifs.

3. The composition of claim 1, wherein $N_3D$ is selected from the group consisting of GpT, GpG, GpA, ApT and ApA.

4. The composition of claim 1, wherein $WN_4$ is selected from the group consisting of TpT or CpT.

5. The composition of claim 1, wherein the immunostimulatory K-type CpG ODN(s) is 10 to 30 nucleotides in length.

6. A pharmaceutical composition comprising an effective amount of 1) an imidazoquinoline having toll-like receptor 7 (TLR7) ligand activity, 2) an immunostimulatory K-type CpG oligodeoxynucleotide (ODN) comprising an unmethylated CpG motif, 3) an antibiotic, and 4) a surfactant, wherein the composition is formulated for topical administration, wherein the amount of the K-type ODN and the imidazoquinoline is sufficient to counteract wound healing delay caused by the antibiotic, and wherein the immunostimulatory K-type CpG ODN comprises the nucleic acid sequence set forth as one of SEQ ID NOs: 3-33.

7. The composition of claim 5, comprising about 250 to 750 μg/gm immunostimulatory K-type CpG ODN.

8. The composition of claim 7, comprising about 500 µg/gm immunostimulatory K-type CpG ODN.

9. The composition of claim 1, wherein the imidazoquinoline having toll-like receptor 7 (TLR7) ligand activity is imiquimod or resiquimod.

10. The composition of claim 5, comprising 5 mg/gm imiquimod.

11. The composition of claim 1, wherein the composition comprises more than one antibiotic.

12. The composition of claim 11, comprising polymixin B, bacitracin and/or neomycin sulfate.

13. The composition of claim 12, comprising about 5,000 to about 10,000 units/gm include Polymyxin B Sulfate, about 1.75 to about 3.5 mg/gm Neomycin Sulfate and about 400 to about 500 units/gm Zinc Bacitracin.

14. The composition of claim 13, comprising about 5 mg neomycin sulfate, 5000 units polymyxin B sulfate and 400 units bacitracin per gram.

15. The composition of claim 1, wherein the surfactant is a polysorbate.

16. The composition of claim 15, wherein the polysorbate is polysorbate 20.

17. The composition of claim 16, wherein the surfactant is 4% to 6% v/v polysorbate 20.

18. The composition of claim 6, comprising:
about 500 µg/gm of the immunostimulatory K-type CpG ODN, about 5 mg neomycin sulfate, 5000 units polymyxin B sulfate and 400 units bacitracin per gram;
about 50 mg/gm imiquimod; and
about 5% weight (w)/w polysorbate 20.

19. The composition of claim 1, formulated for topical ocular administration.

20. A method of accelerating wound healing in a subject, comprising topically administering to the subject a therapeutically effective amount of the composition of claim 1, thereby accelerating wound healing in the subject.

21. The method of claim 20, wherein the subject is a human.

22. The method of claim 20, wherein the wound is a surgical wound or a skin graft.

23. The method of claim 20, comprising topically administering the composition to the skin or eye of the subject.

24. The method of claim 23, wherein the subject has a corneal abrasion and wherein the method comprises topically administering the composition to the eye of the subject.

25. The composition of claim 1, comprising an immunostimulatory K-type CpG ODN comprising the nucleic acid sequence set forth as SEQ ID NO: 11, an immunostimulatory K-type CpG ODN comprising the nucleic acid sequence set forth as SEQ ID NO: 12, and an immunostimulatory K-type CpG ODN comprising the nucleic acid sequence set forth as SEQ ID NO: 29.

26. The composition of claim 6, wherein the imidazoquinoline having toll-like receptor 7 (TLR7) ligand activity is imiquimod or resiquimod.

27. A method of accelerating wound healing in a subject, comprising topically administering to the subject a therapeutically effective amount of the composition of claim 6, thereby accelerating wound healing in the subject.

28. A method of accelerating wound healing in a subject, comprising topically administering to the subject a therapeutically effective amount of the composition of claim 18, thereby accelerating wound healing in the subject.

* * * * *

UNITED STATES PATENT AND TRADEMARK OFFICE
CERTIFICATE OF CORRECTION

PATENT NO.       : 10,076,535 B2
APPLICATION NO.  : 14/397156
DATED            : September 18, 2018
INVENTOR(S)      : Klinman et al.

It is certified that error appears in the above-identified patent and that said Letters Patent is hereby corrected as shown below:

In the Claims

Claim 13, Column 45, Line 13, "about 10,000 units/gm include Polymyxin B Sulfate" should read --about 10,000 units/gm Polymyxin B Sulfate--.

Signed and Sealed this
Sixth Day of April, 2021

Drew Hirshfeld
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 37

<210> SEQ ID NO 1
<211> LENGTH: 32
<212> TYPE: DNA
<213> ORGANISM: Artificial Sequence
<220> FEATURE:
<223> OTHER INFORMATION: Consensus oligodeoxynucleotide
<220> FEATURE:
<221> NAME/KEY: misc_feature
<222> LOCATION: (1)..(3)
<223> OTHER INFORMATION: n is any nucleotide
<220> FEATURE:
<221> NAME/KEY: misc_feature
<222> LOCATION: (4)..(4)
<223> OTHER INFORMATION: n is A or G
<220> FEATURE:
<221> NAME/KEY: misc_feature
<222> LOCATION: (5)..(5)
<223> OTHER INFORMATION: n is C or T
<220> FEATURE:
<221> NAME/KEY: misc_feature
<222> LOCATION: (8)..(8)
<223> OTHER INFORMATION: n is A or G
<220> FEATURE:
<221> NAME/KEY: misc_feature
<222> LOCATION: (9)..(9)
<223> OTHER INFORMATION: n is C or T
<220> FEATURE:
<221> NAME/KEY: misc_feature
<222> LOCATION: (10)..(12)
<223> OTHER INFORMATION: n is any nucleotide
<220> FEATURE:
<221> NAME/KEY: misc_feature
<222> LOCATION: (13)..(22)
<223> OTHER INFORMATION: n is any nucleotide or no nucleotide
<220> FEATURE:
<221> NAME/KEY: misc_feature
<222> LOCATION: (27)..(32)
<223> OTHER INFORMATION: n is G or no nucleotide

<400> SEQUENCE: 1
nnnnncgnnn nnnnnnnnnn nngggggnnnn nn                                32
```

```
<210> SEQ ID NO 2
<211> LENGTH: 10
<212> TYPE: DNA
<213> ORGANISM: Artificial Sequence
<220> FEATURE:
<223> OTHER INFORMATION: consensus oligodeoxynucleotide
<220> FEATURE:
<221> NAME/KEY: misc_feature
<222> LOCATION: (1)..(3)
<223> OTHER INFORMATION: N is any nucleotide
<220> FEATURE:
<221> NAME/KEY: misc_feature
<222> LOCATION: (4)..(4)
<223> OTHER INFORMATION: N is T, G or A
<220> FEATURE:
<221> NAME/KEY: misc_feature
<222> LOCATION: (7)..(7)
<223> OTHER INFORMATION: N is A or T
<220> FEATURE:
<221> NAME/KEY: misc_feature
<222> LOCATION: (8)..(10)
<223> OTHER INFORMATION: N is any nucleotide

<400> SEQUENCE: 2 nnnncgnnnn                                                          10

<210> SEQ ID NO 3
<211> LENGTH: 20
<212> TYPE: DNA
<213> ORGANISM: Artificial Sequence
<220> FEATURE:
<223> OTHER INFORMATION: immunostimulatory oligodeoxynucleotide

<400> SEQUENCE: 3
ataatcgacg ttcaagcaag                                               20

<210> SEQ ID NO 4
<211> LENGTH: 13
<212> TYPE: DNA
<213> ORGANISM: Artificial Sequence
<220> FEATURE:
<223> OTHER INFORMATION: immunostimulatory oligodeoxynucleotide

<400> SEQUENCE: 4
ctcgagcgtt ctc                                                      13

<210> SEQ ID NO 5
<211> LENGTH: 14
<212> TYPE: DNA
<213> ORGANISM: Artificial Sequence
<220> FEATURE:
<223> OTHER INFORMATION: Immunostimulatory oligodeoxynucleotide

<400> SEQUENCE: 5
tctcgagcgt tctc                                                     14

<210> SEQ ID NO 6
<211> LENGTH: 16
<212> TYPE: DNA
<213> ORGANISM: Artificial Sequence
<220> FEATURE:
<223> OTHER INFORMATION: immunostimulatory oligodeoxynucleotide

<400> SEQUENCE: 6
actctggagc gttctc                                                   16

<210> SEQ ID NO 7
<211> LENGTH: 12
<212> TYPE: DNA
```

```
<213> ORGANISM: Artificial Sequence
<220> FEATURE:
<223> OTHER INFORMATION: immunostimulatory oligodeoxynucleotide

<400> SEQUENCE: 7
tgcagcgttc tc                                                              12

<210> SEQ ID NO 8
<211> LENGTH: 12
<212> TYPE: DNA
<213> ORGANISM: Artificial Sequence
<220> FEATURE:
<223> OTHER INFORMATION: immunostimulatory oligodeoxynucleotide

<400> SEQUENCE: 8
tcgaggcttc tc                                                              12

<210> SEQ ID NO 9
<211> LENGTH: 12
<212> TYPE: DNA
<213> ORGANISM: Artificial Sequence
<220> FEATURE:
<223> OTHER INFORMATION: immunostimulatory oligodeoxynucleotide

<400> SEQUENCE: 9
gtcggcgttg ac                                                              12

<210> SEQ ID NO 10
<211> LENGTH: 19
<212> TYPE: DNA
<213> ORGANISM: Artificial Sequence
<220> FEATURE:
<223> OTHER INFORMATION: immunostimulatory oligodeoxynucleotide

<400> SEQUENCE: 10
tcgactctcg agcgttctc                                                       19

<210> SEQ ID NO 11
<211> LENGTH: 20
<212> TYPE: DNA
<213> ORGANISM: Artificial Sequence
<220> FEATURE:
<223> OTHER INFORMATION: immunostimulatory oligodeoxynucleotide

<400> SEQUENCE: 11
atcgactctc gagcgttctc                                                      20

<210> SEQ ID NO 12
<211> LENGTH: 12
<212> TYPE: DNA
<213> ORGANISM: Artificial Sequence
<220> FEATURE:
<223> OTHER INFORMATION: immunostimulatory oligodeoxynucleotide

<400> SEQUENCE: 12
tcgagcgttc tc                                                              12

<210> SEQ ID NO 13
<211> LENGTH: 12
<212> TYPE: DNA
<213> ORGANISM: Artificial Sequence
<220> FEATURE:
<223> OTHER INFORMATION: immunostimulatory oligodeoxynucleotide

<400> SEQUENCE: 13
gtcggcgtcg ac                                                              12
```

```
<210> SEQ ID NO 14
<211> LENGTH: 12
<212> TYPE: DNA
<213> ORGANISM: Artificial Sequence
<220> FEATURE:
<223> OTHER INFORMATION: immunostimulatory oligodeoxynucleotide

<400> SEQUENCE: 14
gtcgacgttg ac                                                           12

<210> SEQ ID NO 15
<211> LENGTH: 16
<212> TYPE: DNA
<213> ORGANISM: Artificial Sequence
<220> FEATURE:
<223> OTHER INFORMATION: immunostimulatory oligodeoxynucleotide

<400> SEQUENCE: 15
actctcgagg gttctc                                                       16

<210> SEQ ID NO 16
<211> LENGTH: 16
<212> TYPE: DNA
<213> ORGANISM: Artificial Sequence
<220> FEATURE:
<223> OTHER INFORMATION: immunostimulatory oligodeoxynucleotide

<400> SEQUENCE: 16
actctcgagc gttctc                                                       16

<210> SEQ ID NO 17
<211> LENGTH: 12
<212> TYPE: DNA
<213> ORGANISM: Artificial Sequence
<220> FEATURE:
<223> OTHER INFORMATION: immunostimulatory oligodeoxynucleotide

<400> SEQUENCE: 17
gtcgtcgatg ac                                                           12

<210> SEQ ID NO 18
<211> LENGTH: 12
<212> TYPE: DNA
<213> ORGANISM: Artificial Sequence
<220> FEATURE:
<223> OTHER INFORMATION: immunostimulatory oligodeoxynucleotide

<400> SEQUENCE: 18
gtcgacgctg ac                                                           12

<210> SEQ ID NO 19
<211> LENGTH: 12
<212> TYPE: DNA
<213> ORGANISM: Artificial Sequence
<220> FEATURE:
<223> OTHER INFORMATION: immunostimulatory oligodeoxynucleotide

<400> SEQUENCE: 19
gtcgacgtcg ac                                                           12

<210> SEQ ID NO 20
<211> LENGTH: 12
<212> TYPE: DNA
<213> ORGANISM: Artificial Sequence
<220> FEATURE:
```

<223> OTHER INFORMATION: immunostimulatory oligodeoxynucleotide

<400> SEQUENCE: 20
gtcatcgatg ca                                                              12

<210> SEQ ID NO 21
<211> LENGTH: 12
<212> TYPE: DNA
<213> ORGANISM: Artificial Sequence
<220> FEATURE:
<223> OTHER INFORMATION: immunostimulatory oligodeoxynucleotide

<400> SEQUENCE: 21
gtcagcgtcg ac                                                              12

<210> SEQ ID NO 22
<211> LENGTH: 11
<212> TYPE: DNA
<213> ORGANISM: Artificial Sequence
<220> FEATURE:
<223> OTHER INFORMATION: immunostimulatory oligodeoxynucleotide

<400> SEQUENCE: 22
tcgagcgttc t                                                               11

<210> SEQ ID NO 23
<211> LENGTH: 16
<212> TYPE: DNA
<213> ORGANISM: Artificial Sequence
<220> FEATURE:
<223> OTHER INFORMATION: immunostimulatory oligodeoxynucleotide

<400> SEQUENCE: 23
actctggagc gttctc                                                          16

<210> SEQ ID NO 24
<211> LENGTH: 16
<212> TYPE: DNA
<213> ORGANISM: Artificial Sequence
<220> FEATURE:
<223> OTHER INFORMATION: immunostimulatory oligodeoxynucleotide

<400> SEQUENCE: 24
actctcgagg gttctc                                                          16

<210> SEQ ID NO 25
<211> LENGTH: 16
<212> TYPE: DNA
<213> ORGANISM: Artificial Sequence
<220> FEATURE:
<223> OTHER INFORMATION: immunostimulatory oligodeoxynucleotide

<400> SEQUENCE: 25
actctcgagc gttcta                                                          16

<210> SEQ ID NO 26
<211> LENGTH: 16
<212> TYPE: DNA
<213> ORGANISM: Artificial Sequence
<220> FEATURE:
<223> OTHER INFORMATION: immunostimulatory oligodeoxynucleotide

<400> SEQUENCE: 26
catctcgagc gttctc                                                          16

```
<210> SEQ ID NO 27
<211> LENGTH: 14
<212> TYPE: DNA
<213> ORGANISM: Artificial Sequence
<220> FEATURE:
<223> OTHER INFORMATION: immunostimulatory oligodeoxynucleotide

<400> SEQUENCE: 27
actctttcgt tctc                                                     14

<210> SEQ ID NO 28
<211> LENGTH: 11
<212> TYPE: DNA
<213> ORGANISM: Artificial Sequence
<220> FEATURE:
<223> OTHER INFORMATION: immunostimulatory oligodeoxynucleotide

<400> SEQUENCE: 28
tcgagcgttc t                                                        11

<210> SEQ ID NO 29
<211> LENGTH: 12
<212> TYPE: DNA
<213> ORGANISM: Artificial Sequence
<220> FEATURE:
<223> OTHER INFORMATION: immunostimulatory oligodeoxynucleotide

<400> SEQUENCE: 29
tcgttcgttc tc                                                       12

<210> SEQ ID NO 30
<211> LENGTH: 15
<212> TYPE: DNA
<213> ORGANISM: Artificial Sequence
<220> FEATURE:
<223> OTHER INFORMATION: immunostimulatory oligodeoxynucleotide

<400> SEQUENCE: 30
gctagacgtt agcgt                                                    15

<210> SEQ ID NO 31
<211> LENGTH: 12
<212> TYPE: DNA
<213> ORGANISM: Artificial Sequence
<220> FEATURE:
<223> OTHER INFORMATION: immunostimulatory oligodeoxynucleotide

<400> SEQUENCE: 31
tcgaggcttc tc                                                       12

<210> SEQ ID NO 32
<211> LENGTH: 21
<212> TYPE: DNA
<213> ORGANISM: Artificial Sequence
<220> FEATURE:
<223> OTHER INFORMATION: immunostimulatory oligodeoxynucletodie

<400> SEQUENCE: 32
tcgtcgtttt tcggtcgttt t                                             21

<210> SEQ ID NO 33
<211> LENGTH: 24
<212> TYPE: DNA
<213> ORGANISM: Artificial Sequence
<220> FEATURE:
<223> OTHER INFORMATION: immunostimulatory oligodeoxynucleotide
```

```
<400> SEQUENCE: 33
tcgtcgtttt gtcgttttgt cgtt                                              24

<210> SEQ ID NO 34
<211> LENGTH: 15
<212> TYPE: DNA
<213> ORGANISM: Artificial Sequence
<220> FEATURE:
<223> OTHER INFORMATION: control oligodeoxynucleotide

<400> SEQUENCE: 34
tagagcttag cttgc                                                        15

<210> SEQ ID NO 35
<211> LENGTH: 12
<212> TYPE: DNA
<213> ORGANISM: Artificial Sequence
<220> FEATURE:
<223> OTHER INFORMATION: control oligodeoxynucleotide

<400> SEQUENCE: 35
ttgagtgttc tc                                                           12

<210> SEQ ID NO 36
<211> LENGTH: 21
<212> TYPE: DNA
<213> ORGANISM: Artificial Sequence
<220> FEATURE:
<223> OTHER INFORMATION: primer

<400> SEQUENCE: 36
actcctacgg gaggcagcag t                                                 21

<210> SEQ ID NO 37
<211> LENGTH: 18
<212> TYPE: DNA
<213> ORGANISM: Artificial Sequence
<220> FEATURE:
<223> OTHER INFORMATION: primer

<400> SEQUENCE: 37
attaccgcgg ctgctggc                                                     18
```